US011272921B2

(12) United States Patent
Anderson

(10) Patent No.: US 11,272,921 B2
(45) Date of Patent: Mar. 15, 2022

(54) SELF-CINCHING SUTURE CONSTRUCT APPARATUS

(71) Applicant: Christian N. Anderson, Nashville, TN (US)

(72) Inventor: Christian N. Anderson, Nashville, TN (US)

(*) Notice: Subject to any disclaimer, the term of this patent is extended or adjusted under 35 U.S.C. 154(b) by 76 days.

(21) Appl. No.: 16/554,546

(22) Filed: Aug. 28, 2019

(65) Prior Publication Data

US 2020/0078010 A1    Mar. 12, 2020

Related U.S. Application Data

(63) Continuation-in-part of application No. 15/937,390, filed on Mar. 27, 2018, which is a continuation of
(Continued)

(51) Int. Cl.
*A61B 17/04* (2006.01)
*A61B 17/06* (2006.01)

(52) U.S. Cl.
CPC ...... *A61B 17/0487* (2013.01); *A61B 17/0401* (2013.01); *A61B 17/06166* (2013.01);
(Continued)

(58) Field of Classification Search
CPC ...... A61B 17/0487; A61B 2017/06185; A61B 2017/0496; A61B 17/0485;
(Continued)

(56) References Cited

U.S. PATENT DOCUMENTS 1,306,369 A    6/1919    Bell
3,409,014 A    11/1968   Shannon
(Continued)

FOREIGN PATENT DOCUMENTS

EP    2455002 A1    5/2012
EP    2462876 A2    6/2012
(Continued)

OTHER PUBLICATIONS

PCT/US2018/041059—International Search Report and Written Opinion, dated Jan. 4, 2019; 9 pages.
(Continued)

*Primary Examiner* — Wade Miles
(74) *Attorney, Agent, or Firm* — Waller Lansden Dortch & Davis, LLP; Matthew C. Cox

(57) ABSTRACT

A suture construct apparatus, including a self-cinching suture member having a first strand, a second strand, a sleeve defined on the second strand, and a self-cinching suture member fixed loop with a sheath positioned on the self-cinching suture member. The suture construct apparatus may further include an anchor disposed on the self-cinching suture member, a self-cinching suture member shuttling suture disposed on the self-cinching suture member fixed loop, and a sheath removably disposed around at least a portion of the self-cinching suture member. The first strand may pass through the sleeve and form a self-cinching suture member free end. The first strand may also be axially moveable through the sleeve.

14 Claims, 50 Drawing Sheets

Related U.S. Application Data application No. 15/783,498, filed on Oct. 13, 2017, now Pat. No. 9,924,939, which is a continuation-in-part of application No. 15/643,173, filed on Jul. 6, 2017, now Pat. No. 10,299,784.

(60) Provisional application No. 62/723,620, filed on Aug. 28, 2018.

(52) U.S. Cl.
CPC ............ *A61B 2017/0404* (2013.01); *A61B 2017/0477* (2013.01); *A61B 2017/0496* (2013.01); *A61B 2017/06185* (2013.01)

(58) Field of Classification Search
CPC .......... A61B 17/06166; A61B 17/0401; A61B 17/0404; A61B 17/0477; A61F 2002/5093; A61F 2002/5095
See application file for complete search history.

(56) References Cited

U.S. PATENT DOCUMENTS

| | | | |
|---|---|---|---|
| 4,291,698 | A | 9/1981 | Fuchs et al. |
| 4,823,794 | A | 4/1989 | Pierce |
| 4,896,366 | A | 1/1990 | Oxman |
| D359,229 | S | 6/1995 | Jules |
| 5,645,588 | A | 7/1997 | Graf et al. |
| 6,066,160 | A | 5/2000 | Colvin et al. |
| 6,660,023 | B2 | 12/2003 | McDevitt et al. |
| 6,716,234 | B2 | 4/2004 | Grafton et al. |
| 7,217,279 | B2 | 5/2007 | Reese |
| 7,235,091 | B2 | 6/2007 | Thornes |
| 7,390,332 | B2 | 6/2008 | Selvitelli et al. |
| D576,867 | S | 9/2008 | Kretz |
| 7,530,999 | B2 | 5/2009 | Clark et al. |
| 7,594,922 | B1 | 9/2009 | Goble et al. |
| 7,601,165 | B2 | 10/2009 | Stone |
| 7,717,929 | B2 | 5/2010 | Fallman |
| 7,862,584 | B2 | 1/2011 | Lyons et al. |
| 7,905,903 | B2 | 3/2011 | Stone et al. |
| 8,109,968 | B2 | 2/2012 | Ashley et al. |
| 8,128,658 | B2 | 3/2012 | Kaiser et al. |
| 8,162,997 | B2 | 4/2012 | Struhl |
| 8,231,674 | B2 | 7/2012 | Albertorio et al. |
| 8,348,960 | B2 | 1/2013 | Michel et al. |
| 8,439,976 | B2 | 5/2013 | Albertorio et al. |
| 8,460,379 | B2 | 6/2013 | Albertorio et al. |
| 8,545,535 | B2 | 10/2013 | Hirotsuka et al. |
| 8,562,645 | B2 | 10/2013 | Stone et al. |
| 8,591,578 | B2 | 11/2013 | Albertorio et al. |
| 8,663,324 | B2 | 3/2014 | Schmieding et al. |
| 8,753,375 | B2 | 6/2014 | Albertorio |
| 8,821,541 | B2 | 9/2014 | Dreyfuss et al. |
| 8,936,621 | B2 | 1/2015 | Denham et al. |
| 9,017,381 | B2 | 4/2015 | Kaiser et al. |
| 9,107,653 | B2 | 8/2015 | Sullivan |
| 9,173,645 | B2 | 11/2015 | Overes et al. |
| 9,179,907 | B2 | 11/2015 | ElAttrache et al. |
| 9,301,745 | B2 | 4/2016 | Dreyfuss |
| 9,345,471 | B2 | 5/2016 | Sullivan |
| 9,381,013 | B2 | 7/2016 | Norton |
| 9,421,007 | B2 | 8/2016 | Brady et al. |
| 9,451,953 | B2 | 9/2016 | Sengun |
| 9,463,013 | B2 | 10/2016 | Pilgeram et al. |
| 9,468,433 | B2 | 10/2016 | Denham et al. |
| 9,481,493 | B2 | 11/2016 | Vantrease |
| 9,498,202 | B2 | 11/2016 | Jafari et al. |
| 9,510,819 | B2 | 12/2016 | Stone et al. |
| 9,615,821 | B2 | 4/2017 | Sullivan |
| 9,642,610 | B2 | 5/2017 | Albertorio et al. |
| 9,706,985 | B2 | 7/2017 | Allen |
| 9,737,292 | B2 | 8/2017 | Sullivan et al. |
| 2005/0187577 | A1* | 8/2005 | Selvitelli ............ A61B 17/0401 606/232 |
| 2007/0083236 | A1 | 4/2007 | Sikora et al. |
| 2009/0105754 | A1 | 4/2009 | Sethi |
| 2010/0256677 | A1 | 10/2010 | Albertorio et al. |
| 2010/0268273 | A1 | 10/2010 | Albertorio et al. |
| 2013/0168478 | A1 | 7/2013 | Holman |
| 2013/0190819 | A1 | 7/2013 | Norton |
| 2013/0345750 | A1 | 12/2013 | Sullivan |
| 2016/0030035 | A1 | 2/2016 | Zajac et al. |
| 2016/0374662 | A1 | 12/2016 | Dreyfuss et al. |
| 2017/0128063 | A1 | 5/2017 | Jackson |
| 2017/0189007 | A1* | 7/2017 | Burkhart ............ A61B 17/0485 |
| 2017/0252033 | A1 | 9/2017 | Dreyfuss et al. |
| 2018/0193015 | A1 | 7/2018 | Denham et al. |

FOREIGN PATENT DOCUMENTS

| | | |
|---|---|---|
| EP | 2572648 A1 | 3/2013 |
| EP | 2581047 A1 | 4/2013 |
| EP | 2724673 A1 | 4/2014 |
| EP | 2777513 A1 | 9/2014 |
| EP | 2263608 B1 | 7/2016 |
| JP | 06114067 A | 4/1994 |
| KR | 1020130092425 | 8/2013 |
| KR | 10-1872802 B1 | 6/2018 |
| WO | 2016149283 A1 | 9/2016 |

OTHER PUBLICATIONS

PCT/US2018/041116—International Search Report and Written Opinion, dated Oct. 17, 2018; 12 pages.
Arthrex; www.arthrex.com; Arthroscopic Stabilization of Acute Acromioclavicular Joint Dislocation Using the TightRope System; Surgical Technique; 2010; six pages.
Rosenberg, Thomas D. MD; Smith & Nephew, Inc., Endoscopy Division, ACL Reconstruction with the ACUFEX Director Drill Guide and EndoButton CL Fixation System; Knee Series, Technique Guide; 12 pages.
Stryker; www.stryker.com; Joint Preservation; VersiTomic G-Lok, 2011; four pages.
DePuySynthes Mitek Sports Medicine, Companies of Johns &Johnson; Rigidloop Adjustable Cortical System Quick Surgical Technique Guide for Soft Tissue ACL Reconstruction; 2014; two pages.
Smith&Newphew; ULTRABUTTON Adjustable Fixation Device; 2016; PN: 71577 Rev. A Feb. 2016; 29 pages.
Takiron Co Ltd., English Abstract of JPH06114067, translation submission date Feb. 8, 2019; 1 page.
Synthes GMBH, Englisth Absliact of KR10-2013-0092425, translation submission date of Nov. 26, 2012; 2 pages.
PCT/US19/048675—International Search Report and Written Opinion, dated Dec. 12, 2019; 15 pages.
Jo Ki Hyun, English Abstract of KR10-1872802B1, English translation; 1 page.

* cited by examiner

SELF-CINCHING SUTURE CONSTRUCT APPARATUS

CROSS-REFERENCES TO RELATED APPLICATIONS

This application is a continuation-in-part of U.S. patent application Ser. No. 15/937,390 filed Mar. 27, 2018 entitled SELF-CINCHING SUTURE CONSTRUCT APPARATUS which is a continuation of U.S. patent application Ser. No. 15/783,498 filed Oct. 13, 2017 entitled SELF-CINCHING SUTURE CONSTRUCT APPARATUS (now U.S. Pat. No. 9,924,939) which is a continuation in part of U.S. patent application Ser. No. 15/643,173 filed Jul. 6, 2017 entitled SUTURE BUTTON CONSTRUCT FOR SURGICAL PROCEDURES, and is a non-provisional of U.S. Provisional Patent Application No. 62/723,620 filed Aug. 28, 2018 entitled SELF-CINCHING SUTURE CONSTRUCT APPARATUS, which are all hereby incorporated by reference in their entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to surgical devices and methods and more particularly to suture devices and methods to secure damaged soft tissue structure.

Various types of sutures, suture fixation devices, and associated methods are known in the art for securing a suture in a desired position and/or at a desired tension during and after surgical procedures. In many surgical procedures, a transosseous hole is drilled through a portion of bone, forming a rigid tunnel for passing a surgical instrument or a suture. The drilled tunnel includes a proximal opening adjacent a tissue repair site where a procedure for the repair of tissue is generally performed, such as but not limited to a procedure to repair a meniscus root tear in a knee. The drilled tunnel generally also includes a distal opening at a location remote from the repair site.

During surgical procedures, one or more sutures are attached to the tissue to be repaired. A free end of the suture is inserted through an opening of the drilled tunnel near the tissue and passed through the tunnel to a tunnel exit. The suture then exits the tunnel and is tensioned to manipulate the damaged tissue into a desired anatomical position. The free end of the suture extending out of the tunnel exit must be pulled tight to maintain tension on the tissue following the operation. After tension is applied, the held in place using an anchor or suture button to maintain the desired tension.

Numerous types of sutures, suture buttons, and suture anchors are known in the art for tying off sutures on the distal end of transosseous tunnels for maintaining tension. However, such conventional sutures, suture buttons, and suture anchors are often inadequate and may lead to unintentional release of the applied tension on the suture over time. This release of tension may cause the tissue to heal improperly, leading to discomfort and pain at the joint and potentially requiring additional operations to reapply the necessary tension.

For example, with regard to conventional sutures, such devices for meniscus root repair and other operations on the knee have a disadvantage of requiring one or more knots on the outside of the drill tunnel opening to secure the soft tissue in place. The knots may rub against the soft tissue, causing discomfort or irritation. Likewise, knots positioned near the drill tunnel exit also cause discomfort and irritation.

Additionally, when the suture is pulled tight to reduce the soft tissue to its desired anatomical position, the suture has a tendency to allow the button to move slightly away from the bone. The button may also inadvertently move away from the bone when a knot is tied in the suture at the button site. Any gap between the button and the bone may result in a loss of tension in the suture.

Further, knotted suture constructs for meniscus root repair may slip or loosen over time as knots work loose. Such loosening of knotted suture constructs may cause damage to the tissue, improper healing, and further injury.

What is needed, then are improvements in suture construct devices and methods for surgical procedures.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a suture construct apparatus, including a self-cinching suture member having a first strand, a second strand, a sleeve defined on the second strand, and a self-cinching suture member fixed loop. The suture construct apparatus may further include a sheath removably disposed around at least a portion of the self-cinching suture member. The first strand may pass through the sleeve and form a self-cinching suture member free end. The first strand may be axially moveable through the sleeve.

Another aspect of the disclosure is a suture construct apparatus, including a self-cinching suture member including a first strand, a second strand, a sleeve defined on the second strand and a self-cinching suture member fixed loop. The suture construct apparatus may further include a continuous loop device disposed on the first strand, a continuous-loop shuttling suture disposed on the continuous loop, and a self-cinching suture member shuttling suture disposed on the self-cinching suture member fixed loop. The first strand may pass through the sleeve and form a self-cinching suture member free end. The first strand may be axially moveable through the sleeve.

A further aspect of the disclosure is a suture construct apparatus, including a self-cinching suture member including a first strand, a second strand, a sleeve defined on the second strand and a self-cinching suture member fixed loop. The suture construct apparatus may further include an anchor disposed on the first strand of the of the self-cinching suture member. The first strand may pass through the sleeve and form a self-cinching suture member free end. The first strand may be axially moveable through the sleeve.

Numerous other objects, advantages, and features of the present disclosure will be readily apparent to those of skill in the art upon a review of the following drawings and description of a preferred embodiment.

DETAILED DESCRIPTION

Figure 1:
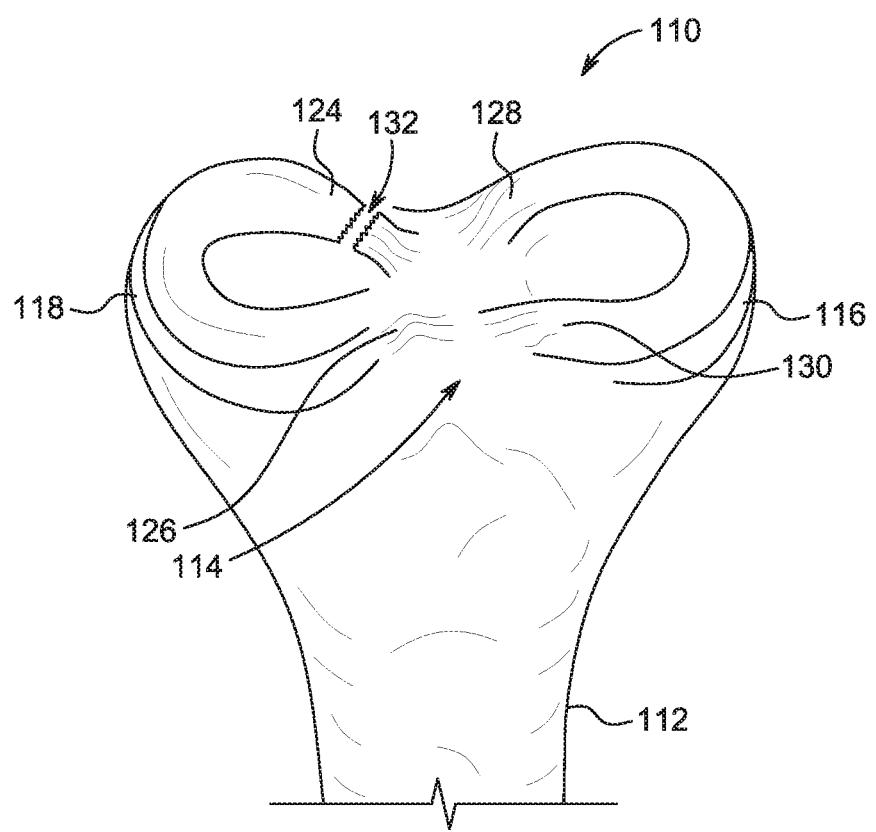
FIG. 1 illustrates a perspective view of an embodiment of a portion of knee including a meniscal root tissue injury.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The present disclosure provides a self-cinching suture construct for use in surgical procedures, including but not limited to operations on the knee. As shown in FIG. 1, an embodiment of a knee 110 showing the upper end of a tibia 112 including a medial meniscus 116 and a lateral meniscus 118. The medial meniscus 116 includes a posterior root 128 and an anterior root 130. The lateral meniscus 118 includes a posterior root 124 and an anterior root 126. Each root is attached to the tibia at local tissue attachment sites along the tibial plateau 114. Various types of injuries may lead to one or more root tears or injuries in the lateral or medial meniscus. An example of a root tear 132 on the lateral posterior root 124 is shown in FIG. 1.

Although various figures refer to an exemplary lateral posterior root tear injury, the devices and methods of the present disclosure are applicable to many different types of injuries, including but not limited to tears and injuries in the anterior lateral meniscus and posterior lateral meniscus as well as the anterior medial meniscus and posterior medial meniscus. The examples demonstrating application to a lateral posterior meniscus root tear are offered only as a non-limiting example. Likewise, one skilled in the art will recognize other implementations of the devices and methods disclosed herein for use in other surgical procedures beyond those relating to the meniscus.

Figure 2:
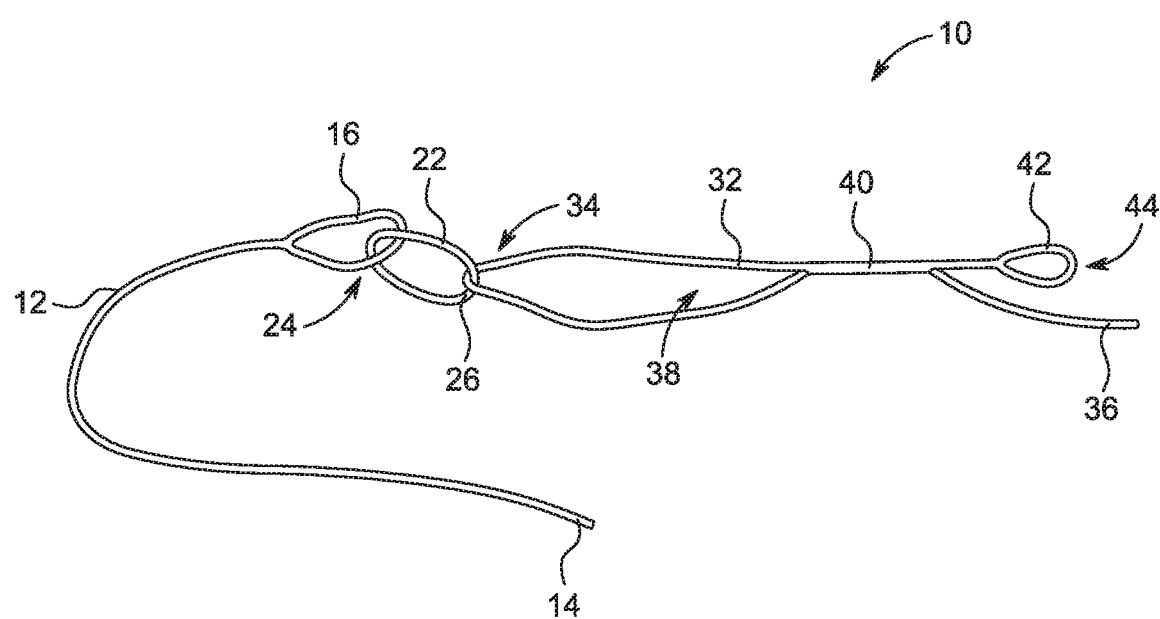
FIG. 2 is a perspective view of an embodiment of a self-cinching suture construct apparatus in accordance with the present disclosure.

The present disclosure generally provides a self-cinching, knotless suture construct device for repairing a meniscus root tear in a knee. As shown in FIG. 2, an embodiment of a suture construct device 10 is illustrated. The suture material may include any suitable suture material known in the art. The device 10 includes a meniscal end and a button end. The meniscal end is generally secured to the damaged meniscus and is operable to reduce the damaged meniscus to the appropriate anatomical position to allow healing and prevent further damage. The button end is generally securable to a suture button. When the device 10 is secured to the meniscus at the meniscal end and the suture button at the button end, the device 10 may be positioned through a transosseous tunnel 138 in a patient's bone during a meniscal root tear repair procedure, for example.

The device 10 may generally include a continuous loop 22 and a self-cinching suture member 32. The device may likewise implement an anchor 21 in place of the continuous loop 20, and the anchor may include a variety of embodiments, which will be discussed in further detail later in this description. The self-cinching suture member 32, or knotless repair suture 32, may generally include a self-cinching suture leading end 34 positioned on a forward end toward the continuous loop 22.

Referring further to FIG. 2, a self-cinching suture sleeve 40 is disposed on the self-cinching suture member 32. In some embodiments, self-cinching suture member 32 is constructed of a suture material having an annular cross-sectional profile, forming an elongated tube. Such suture material may include braided or non-braided suture material. In some embodiments, self-cinching suture sleeve 40 is defined within the interior hollow body of the suture material.

For example, a self-cinching suture member free end 36 may be passed through a self-cinching suture sleeve segment 40 of the self-cinching suture member body, as shown in FIG. 2. The segment of the suture body surrounding the passed-through portion forms a self-cinching suture sleeve 40 around the suture strand of the self-cinching suture member free end 36.

Thus, a portion of the suture strand between the self-cinching suture member free end 36 and the self-cinching suture leading end 34 may slide through the self-cinching suture sleeve 40. As tension is applied to the suture member, the self-cinching suture sleeve 40 may tighten around the suture strand passing through self-cinching suture sleeve 40, thereby securing or locking the suture strand in place relative to the self-cinching suture sleeve 40. The self-cinching suture sleeve 40 provides a clamping effect against the strand of suture material passing through the self-cinching suture sleeve 40. The clamping effect prevents the strand from inadvertently loosening during use. More specifically, during use, when the self-cinching suture member 32 is pulled tight, the self-cinching suture sleeve 40 restricts axial translation of the self-cinching suture member free end 36. As such, the suture member may be referred to as a "self-cinching" or "knotless" suture construct.

Referring further to FIG. 2, another feature of the self-cinching suture member 32 includes a retaining structure such as a self-cinching suture fixed loop 42 formed at the self-cinching suture trailing end 44. During a surgical procedure, a suture button 270 or suture anchor may be secured to the device 10 at the self-cinching suture fixed loop 42. The application of tension to self-cinching suture member free end 36 causes the self-cinching suture member 32 to be generally drawn back toward the continuous loop 20. This motion effectively forms an adjustable loop 38 which closes as tension is applied.

As various embodiments of the device will be discussed herein, the discussion will be divided into separate sections disclosing general embodiments. Each general embodiment includes various other embodiments and features that will be discussed in each respective section. Some of these general embodiments include a sheathed device 210 and double shuttling suture device 310. Further, each embodiment of the device 10 may implement various embodiments of an anchor 21 in place of the continuous loop 20.

Figure 3:
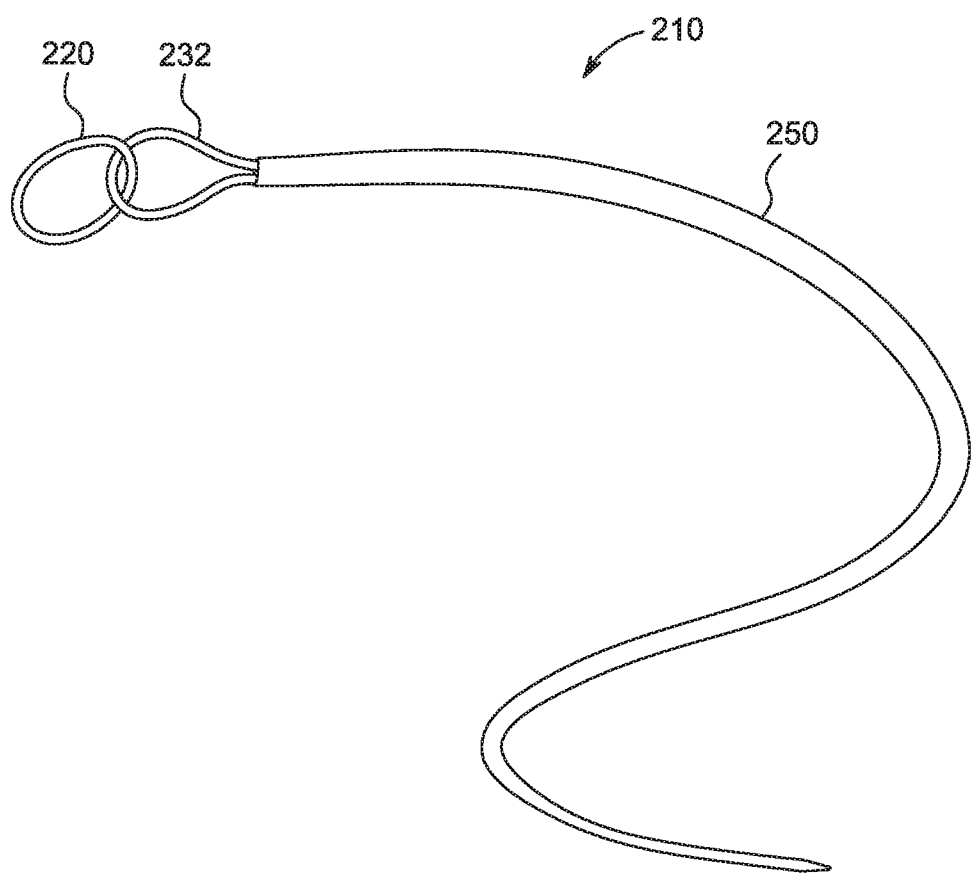
FIG. 3 is a perspective view of an embodiment of a self-cinching suture construct apparatus having a sheath.

One embodiment of the suture construct device 10 includes a sheathed device 210. FIGS. 3 and 4 demonstrate an exemplary embodiment of a sheathed device 210. As seen in FIG. 3, the sheathed device may generally include a continuous loop 220, a self-cinching suture member 232, and a sheath 250. The continuous loop 220 may also be substituted with a variety of anchors 221, which will be discussed in further detail, but is generally coupled to the self-cinching suture member 232. For example, FIGS. 4B-4I demonstrate a self-cinching suture member 232 implementing various embodiments of anchors 221. As seen in FIG. 3, the sheath 250 may cover at least a portion of the self-cinching suture member 232.

Figure 4A:
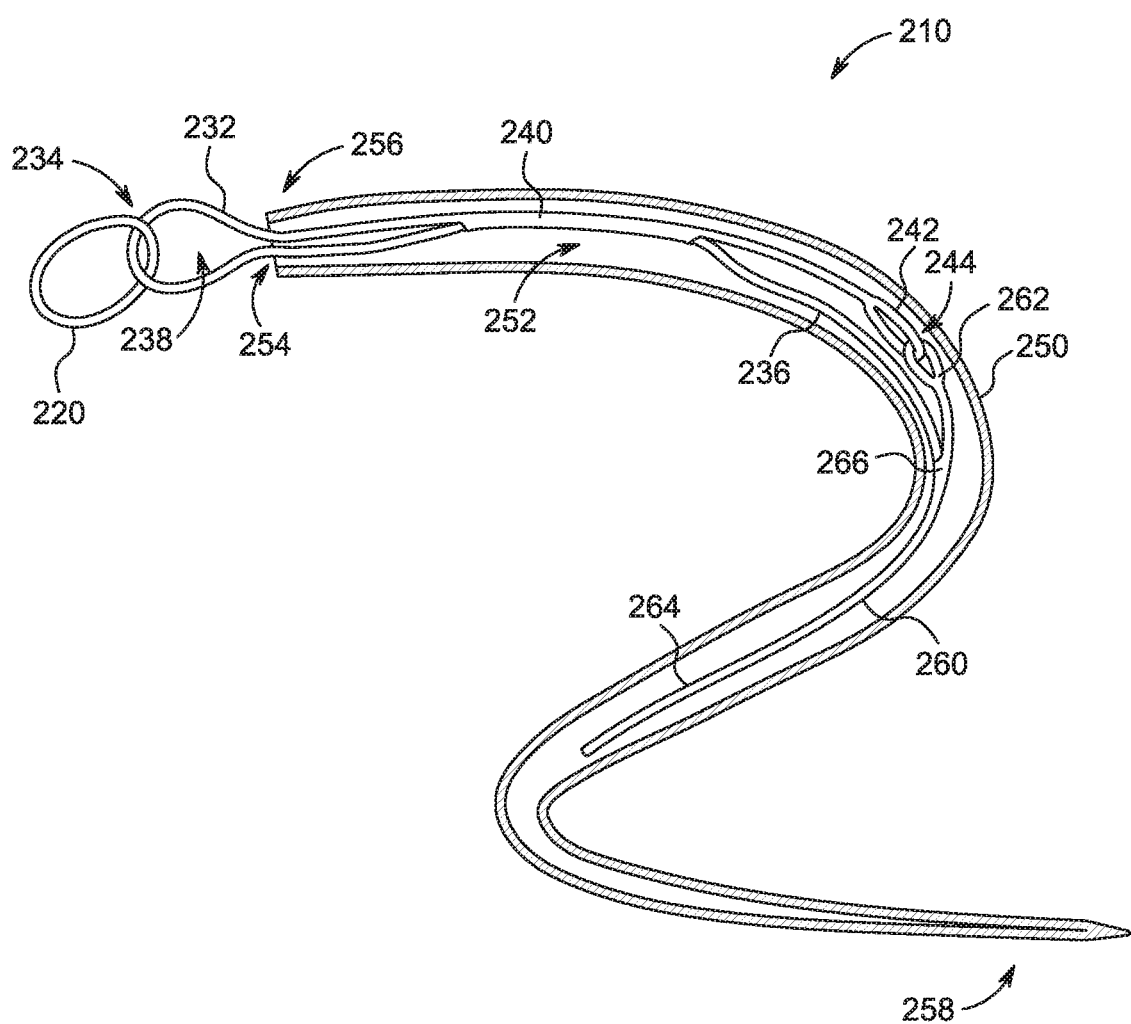
FIGS. 4A-4I are sectional views of various embodiments of a self-cinching suture construct apparatus having a sheath and various anchors.
Figure 4B:
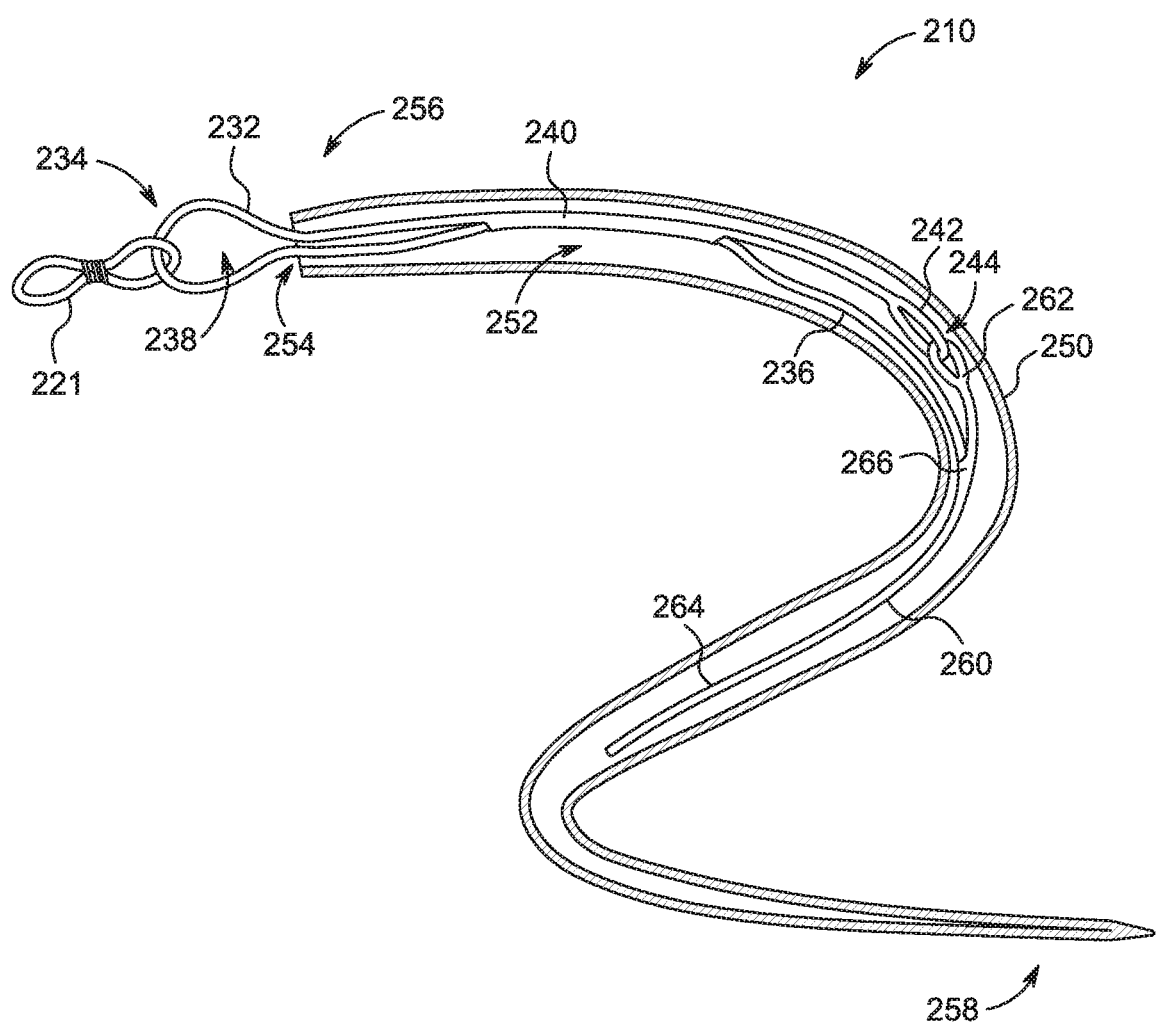
Figure 4C:
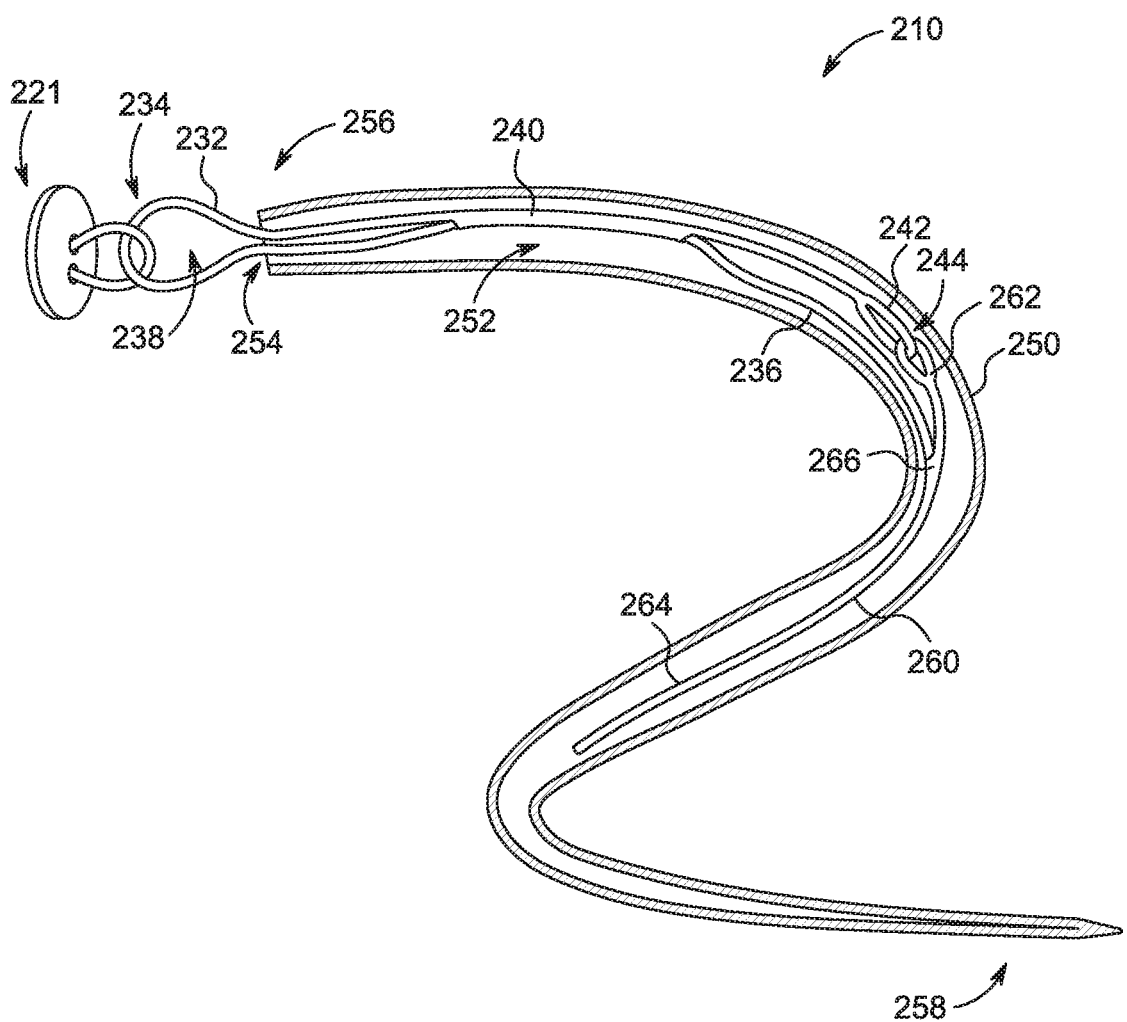
Figure 4D:
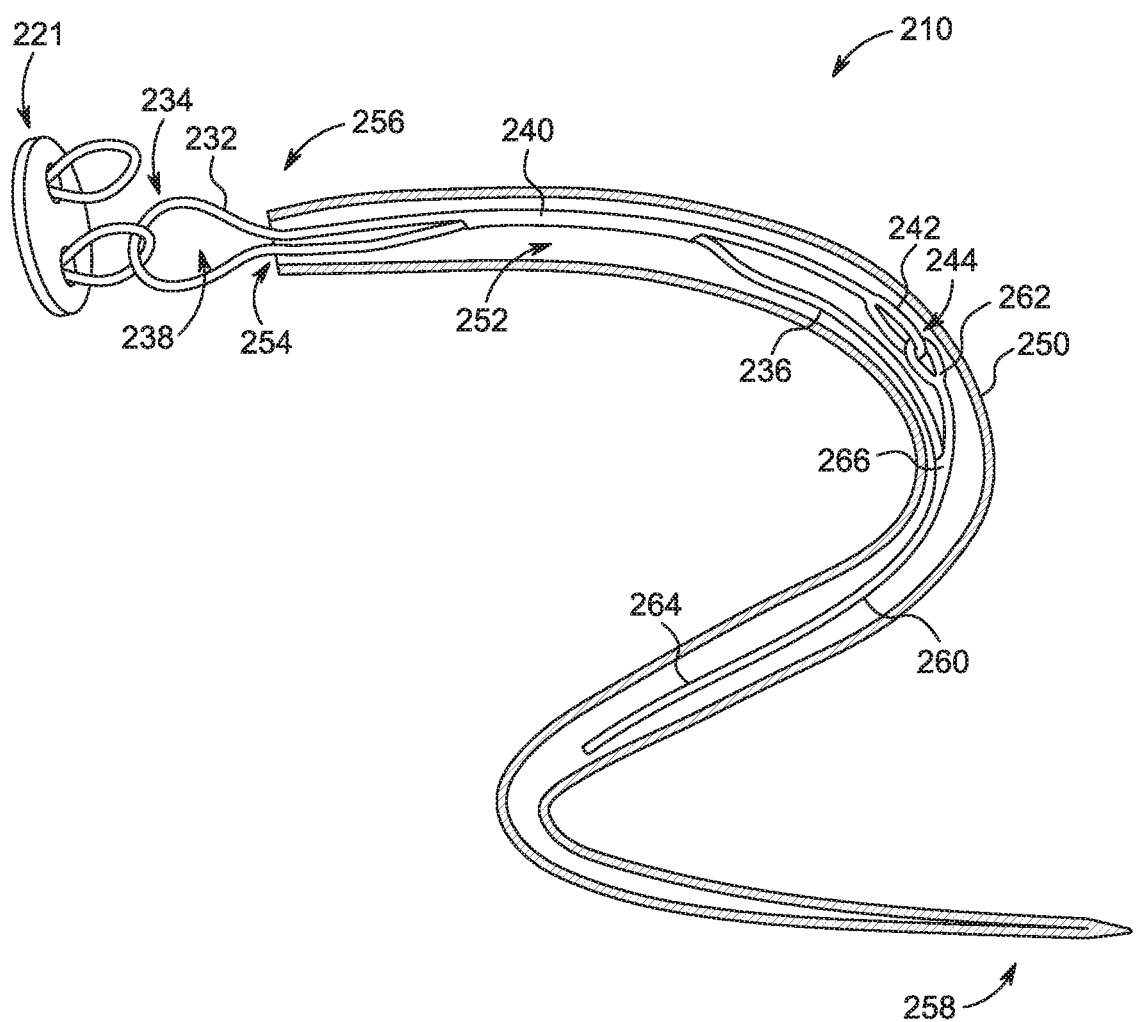
Figure 4E:
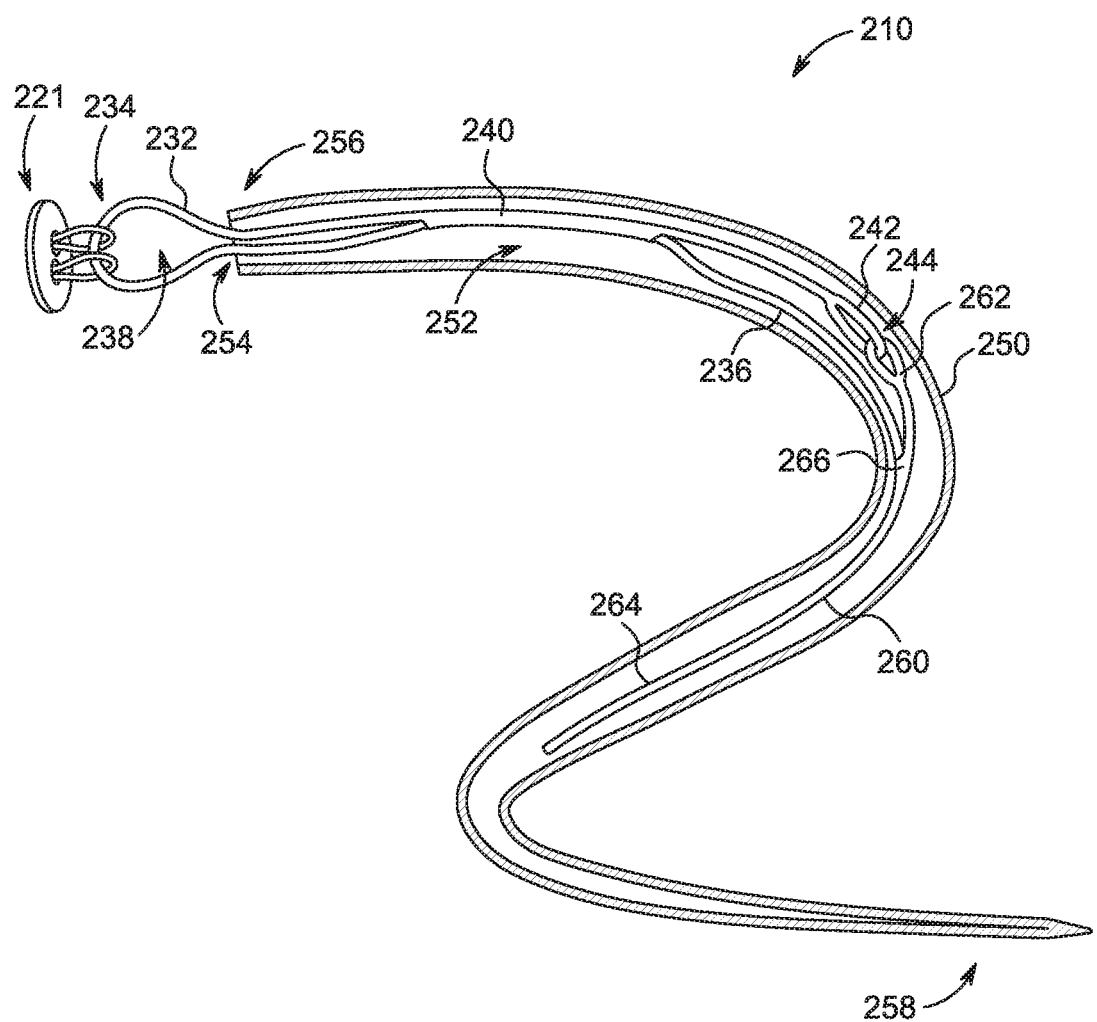
Figure 4F:
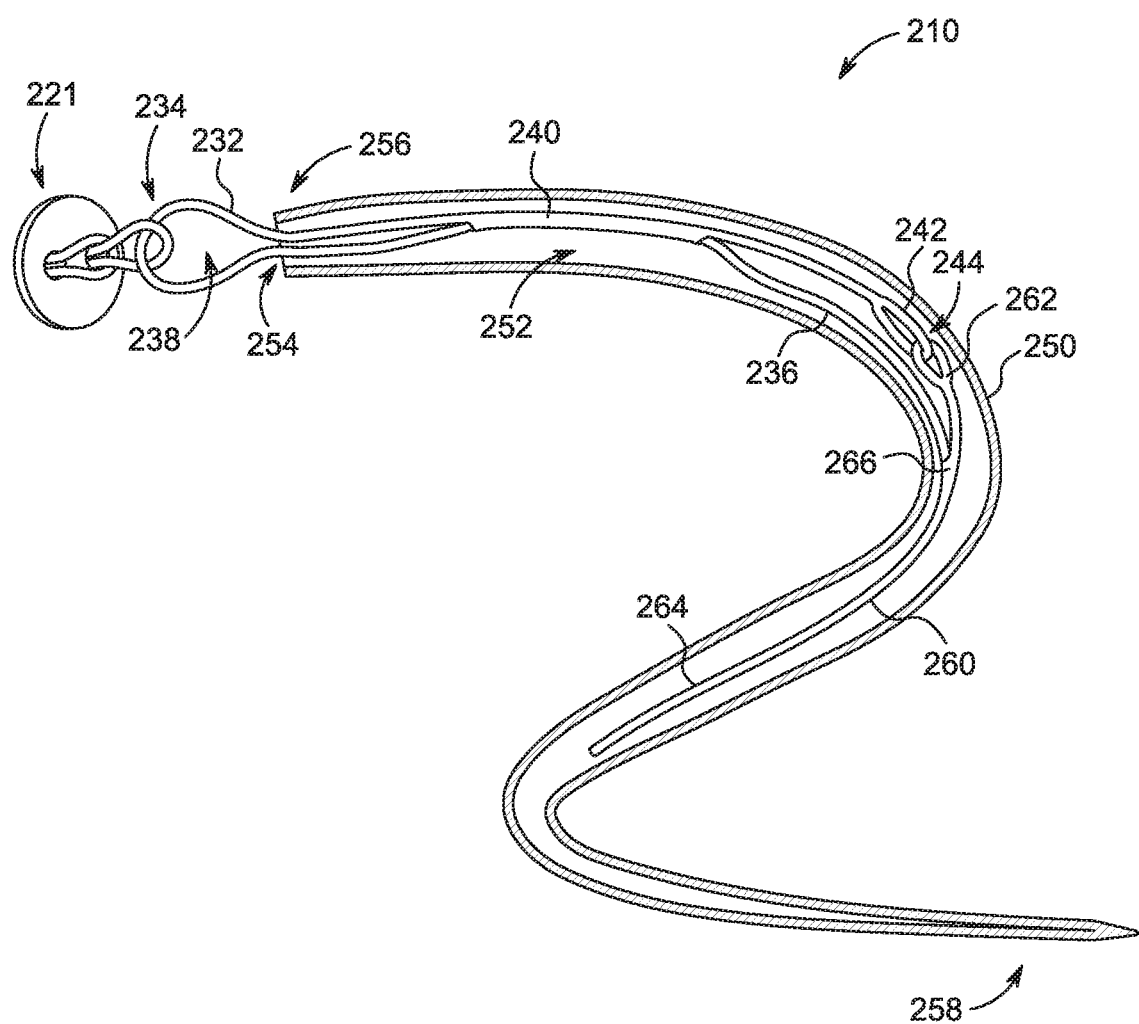
Figure 4G:
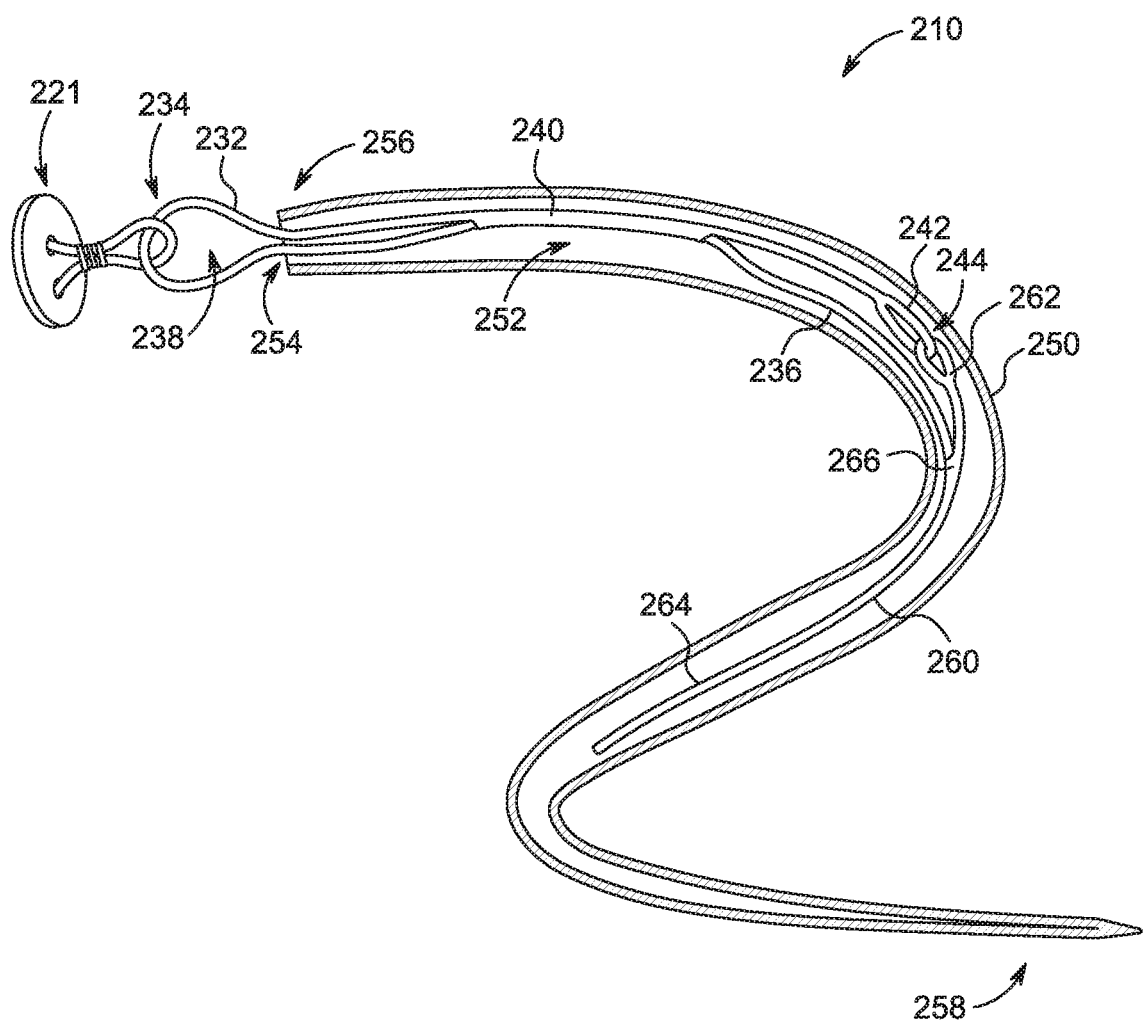
Figure 4H:
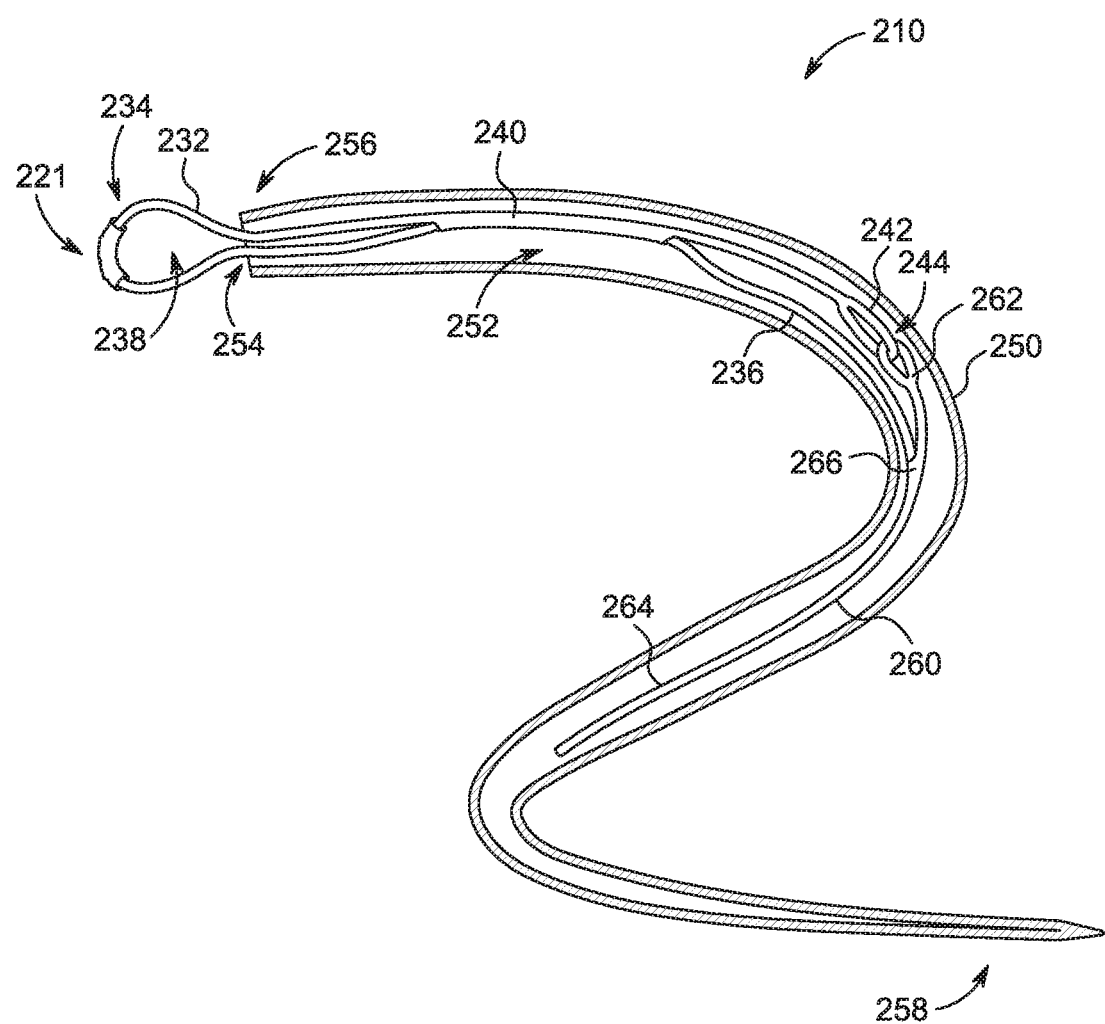
Figure 4I:
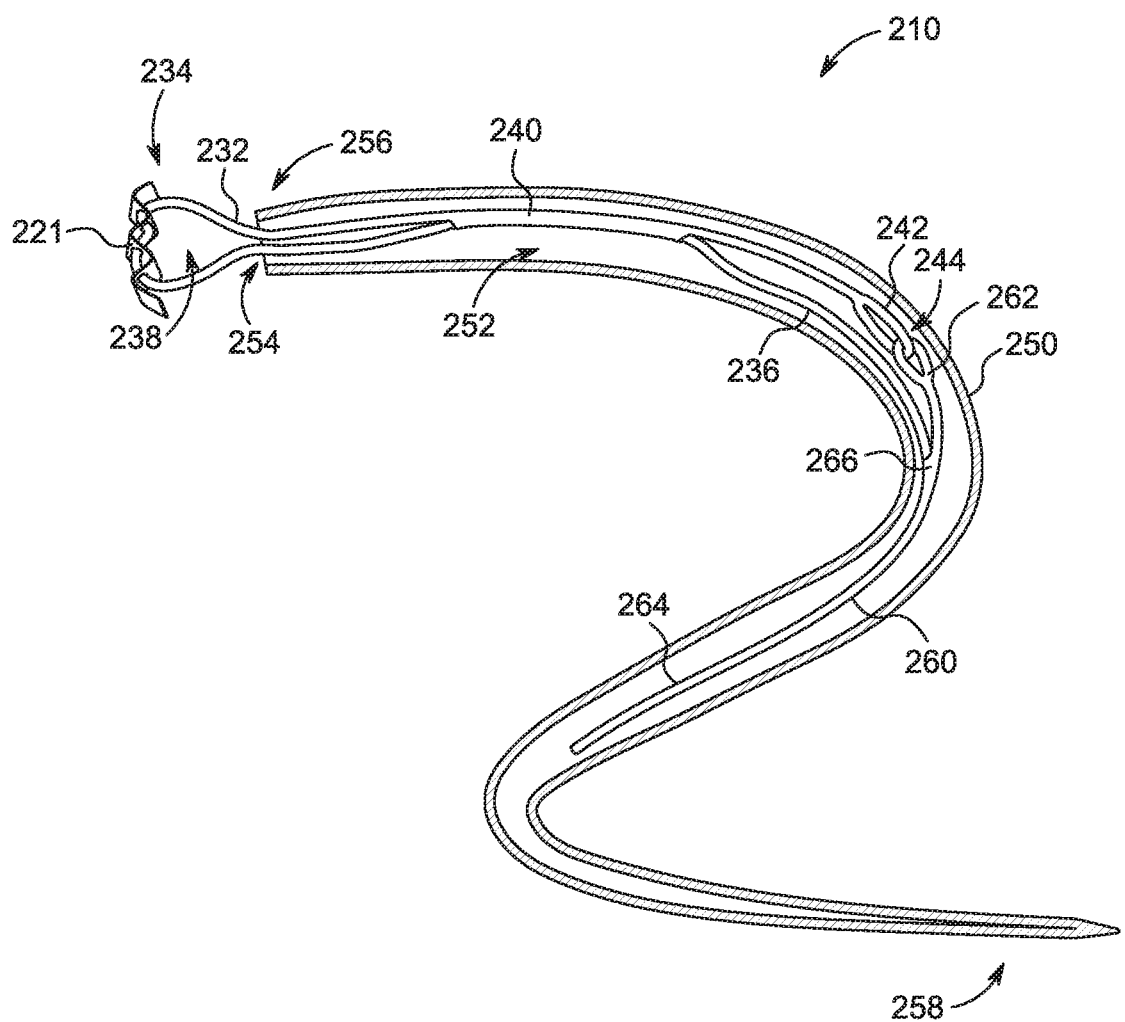

Referring now to FIG. 4A, in some embodiments, the self-cinching suture member 232 includes a self-cinching suture leading end 234 positioned on a forward end toward the continuous loop 220, a self-cinching suture sleeve 240 is disposed on the self-cinching suture member 232, and a self-cinching suture member free end 236. The self-cinching suture member free end 236 may be passed through the self-cinching suture sleeve 240. Thus, a portion of the suture strand between the self-cinching suture member free end 236 and the self-cinching suture leading end 234 may slide through the self-cinching suture sleeve 240 and the portion forming an adjustable loop 238.

The self-cinching suture member 232 may also include a self-cinching suture fixed loop 242 formed at the self-cinching suture trailing end 244, the fixed loop 242 operable to retain a suture button 270 or suture anchor. The fixed loop 242 may also be coupled to a sacrificial suture 260. The sacrificial suture 260 may include a coupling portion 262 for coupling to the fixed loop 242 of the self-cinching suture member 232 and a sacrificial suture strand 264. The sacrificial suture strand 264 may be operable to allow a user to grasp and manipulate the device 10 for ease of use. The sacrificial suture 260 may also include a retaining portion 266. The retaining portion 266 may be operable to retain a portion of the self-cinching suture member free end 236. The retaining portion 266 allows for the device 10 to have the profile of one continuous strand, minimizing the loose ends to the two loose ends of the strand. Having only two loose ends may be beneficial specifically in application in which the device is to be inserted or threaded into another device or space, such as damaged tissue of a patient.

With further reference to FIG. 4, the sheath 250 may be installed on the self-cinching suture member 232. The sheath 250 may comprise a structure formed of a variety of materials, including similar suture materials as used in the various other portions of the suture construct device 10. The sheath 250 may form a hollow interior 252 with an opening 254 formed at a proximate end 256 of the sheath 250. In some embodiments, the sheath may have a second opening at a distal end 258 of the sheath 250. The hollow interior 252 and the open end 254 are shaped to receive and retain at least a portion of the self-cinching suture member 232. In some embodiments, the sheath 250 may retain the self-cinching suture leading end 234, the self-cinching suture sleeve 240, the self-cinching suture member free end 236, the self-cinching suture fixed loop 242, and the sacrificial suture 260. A portion of the self-cinching suture member 232 may be exposed because the sheath 250 may not retain the entire self-cinching suture member 232. For example, the adjustable loop 238 of the self-cinching suture member 232 and the continuous loop 220 are not retained in the sheath 250. In some embodiments, the sheath 250 is tapered.

FIGS. 5A-5I demonstrate an exemplary embodiment of the sheathed device 210 being installed onto a meniscal root 124. The distal end 258 of the sheath 250 is inserted through the meniscal root 124 either through a pre-formed hole or is inserted via a secondary device such as a needle or any other device as known by one of skill in the art. When the distal end 258 of the sheath has been inserted through the meniscal root 124, the sheathed device 210 may be advanced through the meniscal root 124. In those embodiments in which the sheath 250 is tapered, the hole in the meniscal root 124 may be dilated via the sheath 250 to the appropriate size to accommodate the sheathed device 210 and prevent tear out. The sheath 250 may also be operable to provide a smooth surface for passing the sheathed device 210 through the meniscal root 124 without various components of the self-cinching suture member 232 catching in the meniscal root 124. As such, the exterior surface of the sheath 250 may comprise a smooth surface operable to provide minimal friction between the sheath 250 and the meniscal root 124.

Figure 5A:
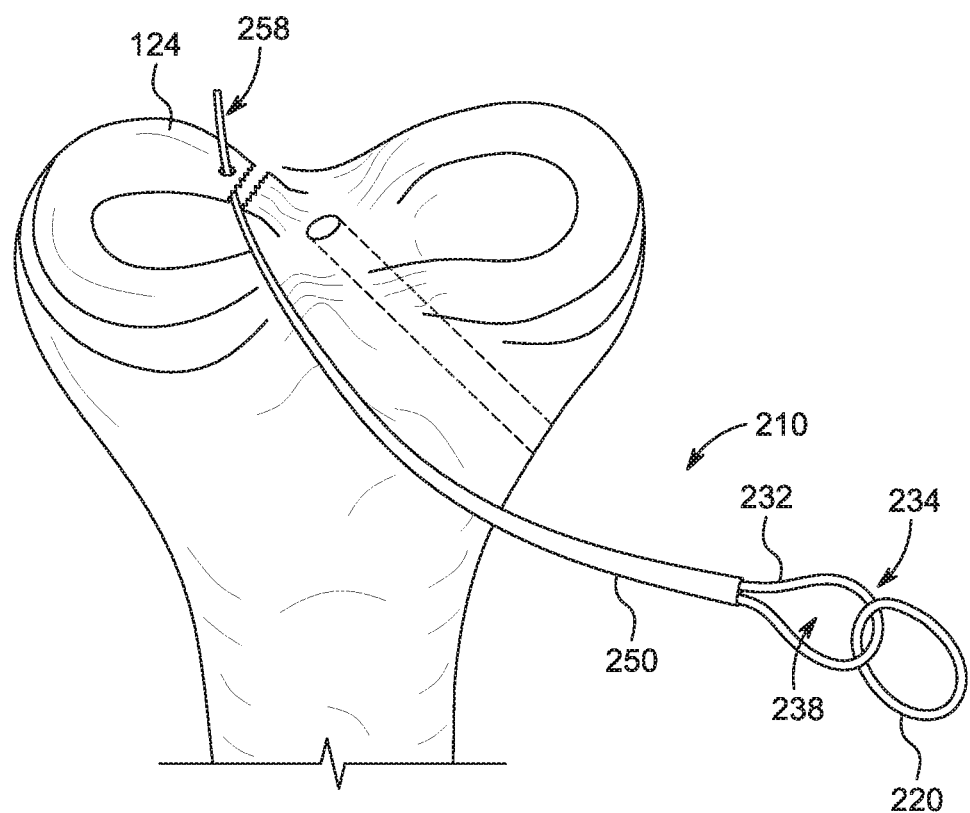
FIGS. 5A-5I illustrates an exemplary method of using a self-cinching suture construct apparatus having a sheath.
Figure 5B:
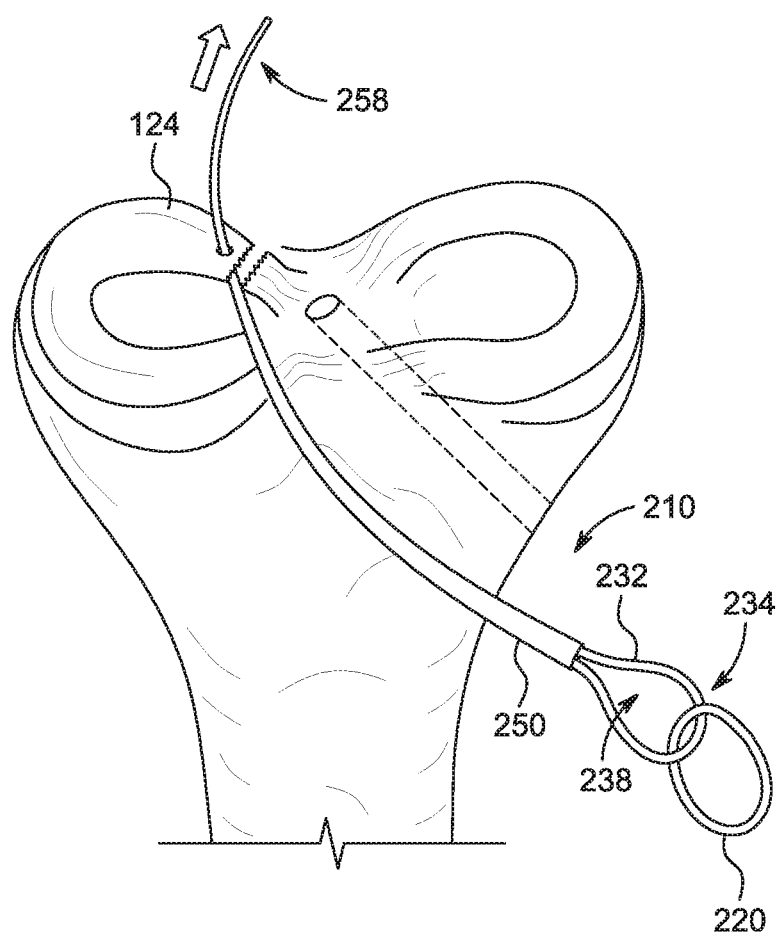
Figure 5C:
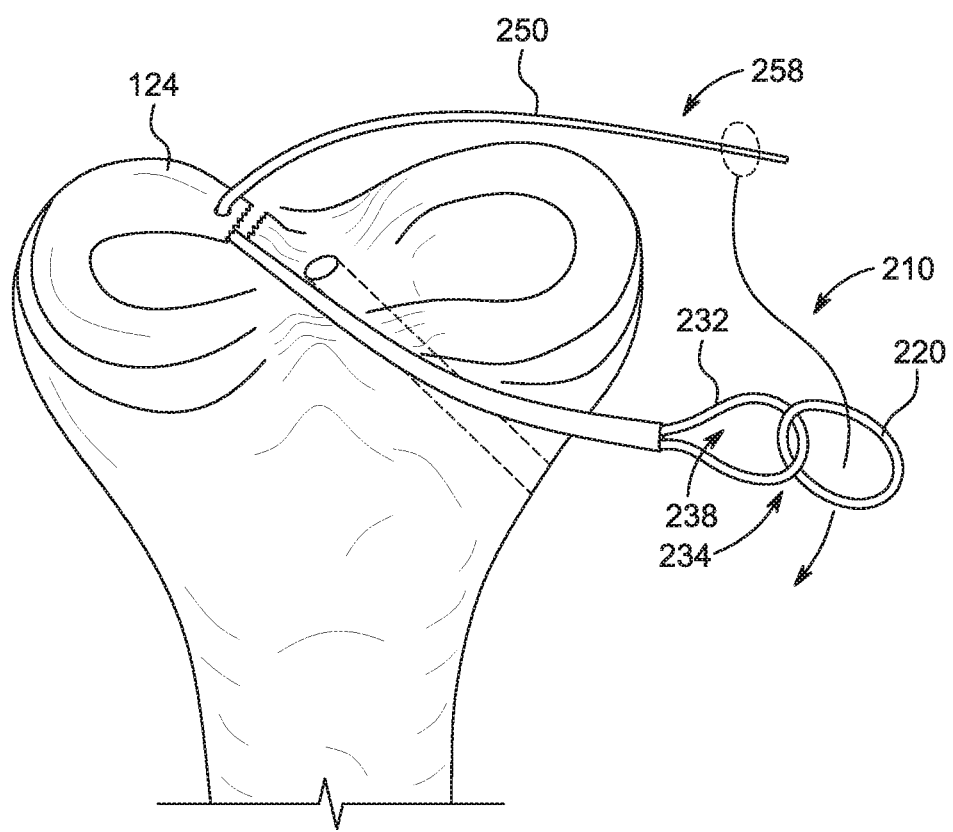

As seen in FIG. 5C, the distal end 258 of the sheath 250 may be inserted through the continuous loop 220. In this embodiment, a continuous loop 220 is implemented for securing sheathed device 210 to the damaged tissue. Inserting the distal end 258 of the sheath 250 through the continuous loop 220 allows the sheathed device 210 to form a girth hitch around the meniscal root 124 to secure the sheathed device 210 to the meniscal root 124. In those embodiments in which an anchor 221 is implemented, the step of passing the distal end 258 of the sheath 250 through the continuous loop 220 is not necessary. In those embodiments in which the anchor 221 is implemented, the sheath 250 may be advanced through the meniscal root 124 until the anchor 221 engages the meniscal root 124, thus providing simple installation of the sheathed device 210.

Figure 5D:
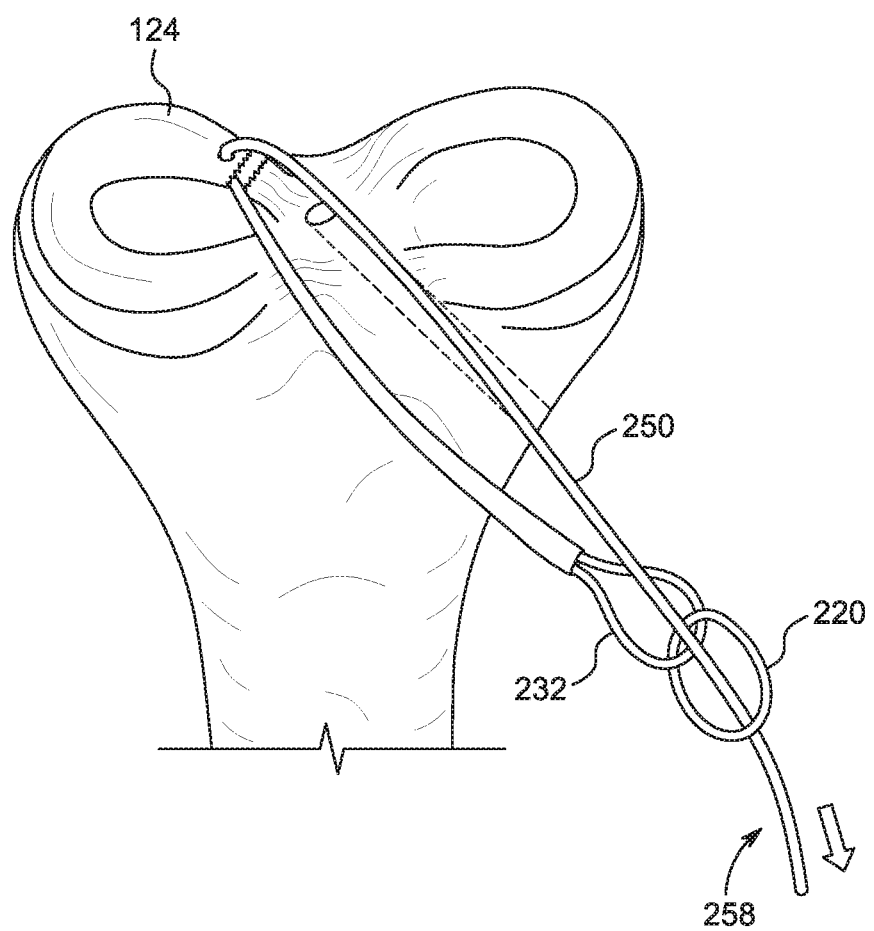
Figure 5E:
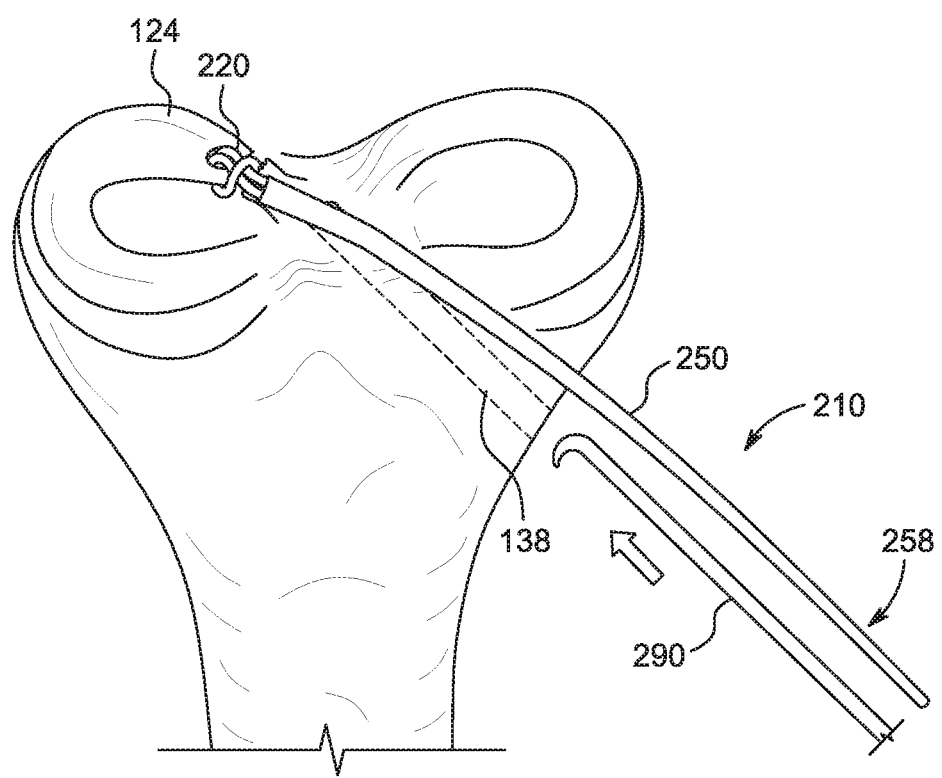

Referring now to FIG. 5D, when the distal end 258 of the sheath 250 is passed through the continuous loop 220, the distal end 258 may be tensioned such that the sheath 250 and the sheathed device 210 generally advance through the meniscal root 124 until a girth hitch is formed on the meniscal root 124, as seen in FIG. 5E. Generally, by inserting the distal end 258 of the sheath 250 and advancing the sheathed device 210 through the damaged tissue, the sheathed device 210 is only passing through the damaged tissue in one direction (one-step passage) and minimizes the contact between the sheathed device 210 and the damaged tissues.

Figure 5F:
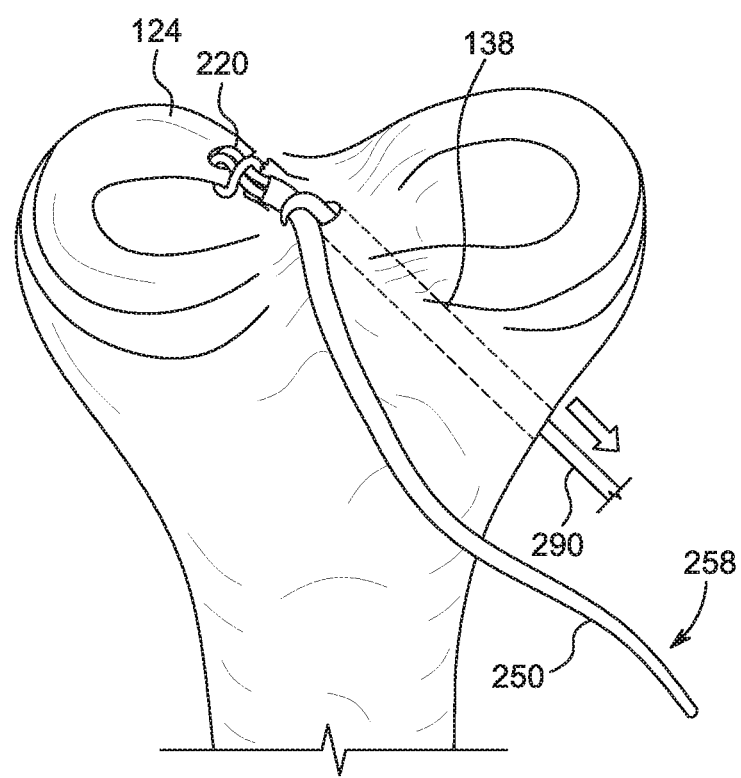
Figure 5G:
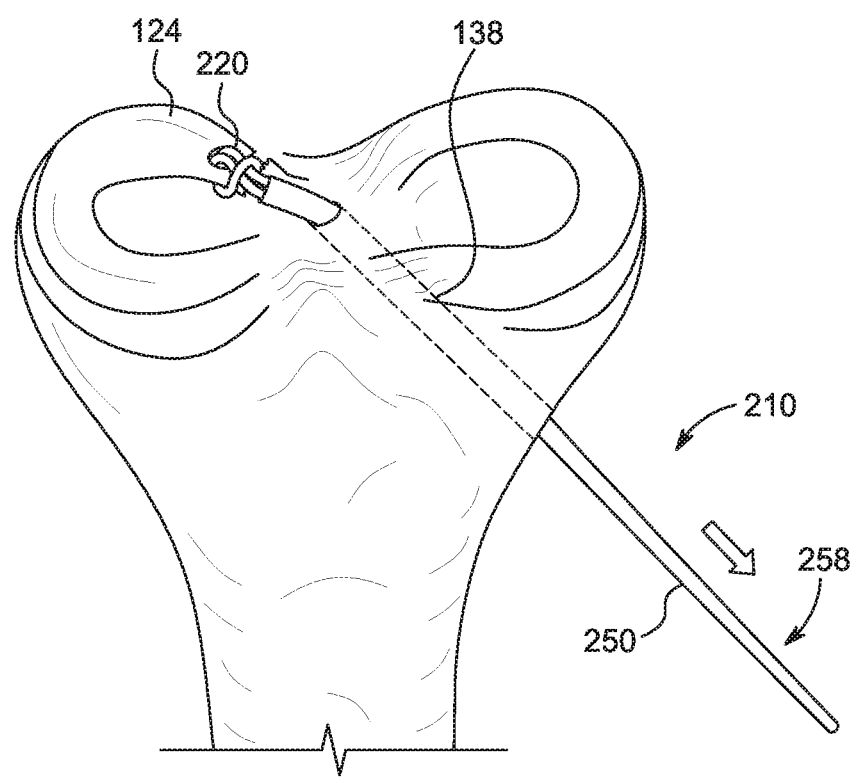

Once the sheathed device 210 is secured to the damaged tissue, a grabbing device 290 may be passed through a transosseous tunnel 138 bored through the patient's tibia in order to secure the sheathed device 210. In some embodiments, the grabbing device 290 may include a looped nitinol wire or a hook. The grabbing device 290 may retain a portion of the sheathed device 210 such that when the grabbing device 290 is retracted from the transosseous tunnel, the sheathed device 210 is shuttled through the transosseous tunnel, as seen in FIGS. 5F and 5G.

Figure 5H:
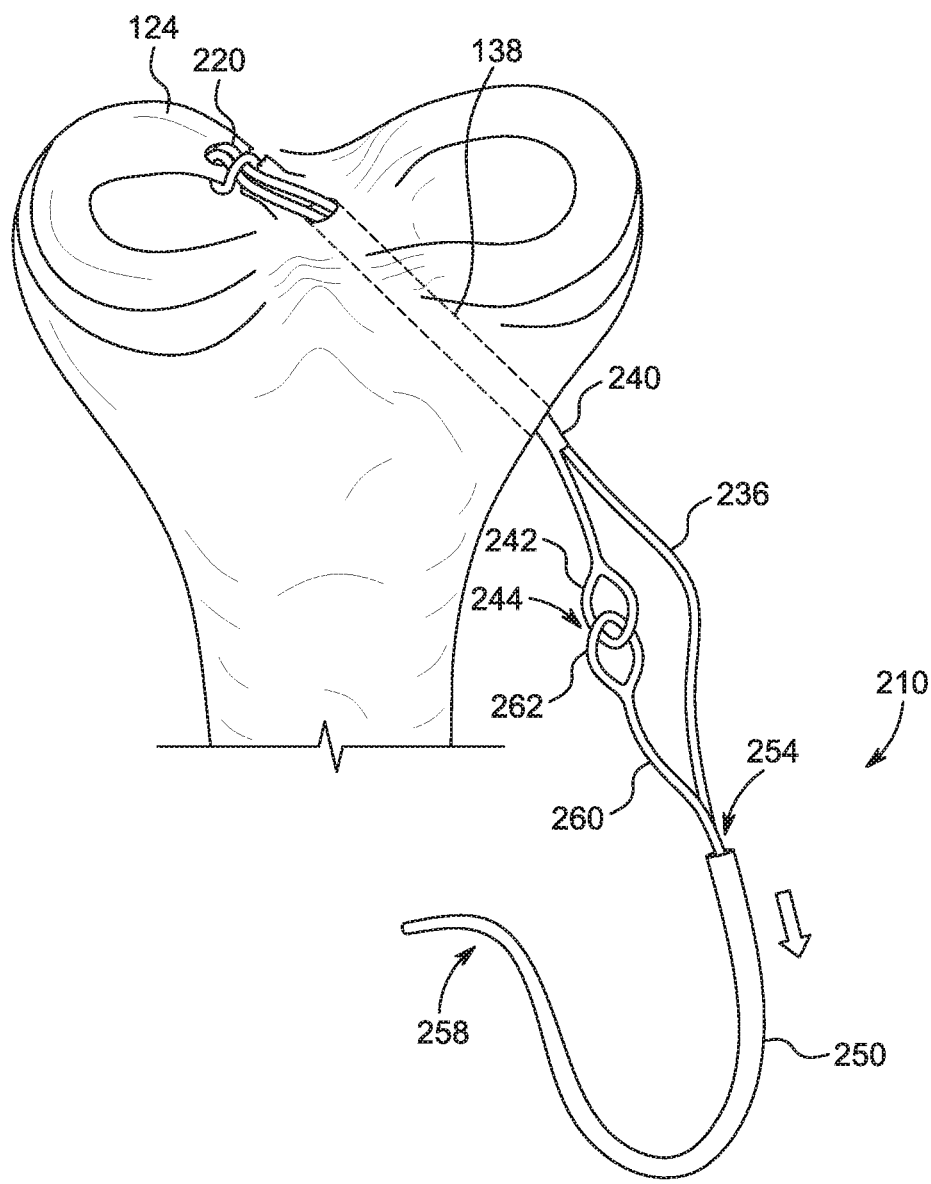
Figure 5I:
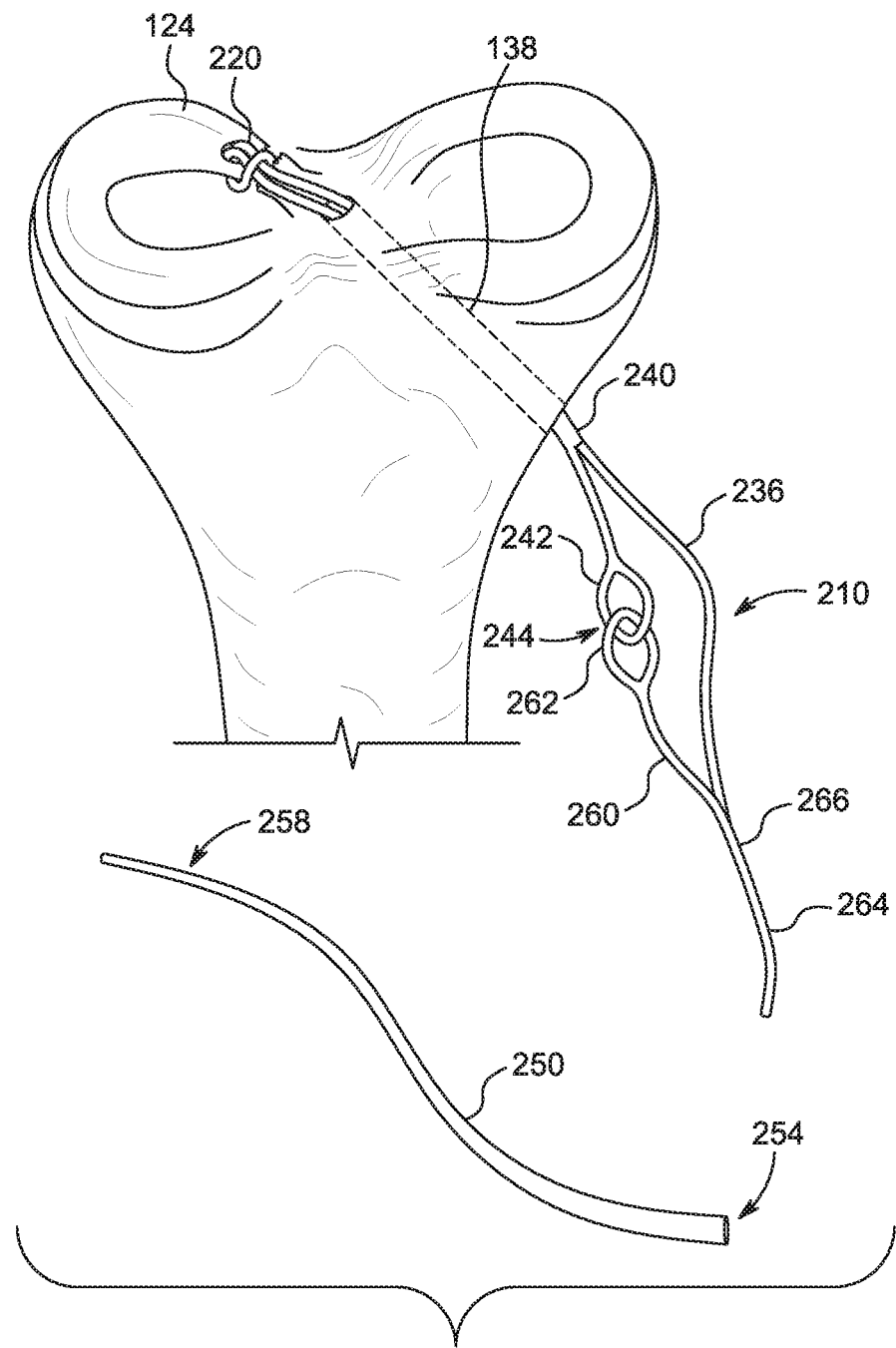

Now referring to FIG. 5H, once the sheathed device 210 is secured to the damaged tissue and shuttled through the transosseous tunnel, the sheath 250 may be removed from the self-cinching suture member 232. After the self-cinching suture member 232 has been exposed, the self-cinching suture member 232 may be secured to a suture button 270 or suture anchor such that the damaged tissue (meniscal root 124 as shown in FIG. 5) is reduced to an anatomical position to promote healing and repair and to prevent further injury to the tissue. The securing of the self-cinching suture member 232 will be described in greater detail later in this description.

Figure 6A:
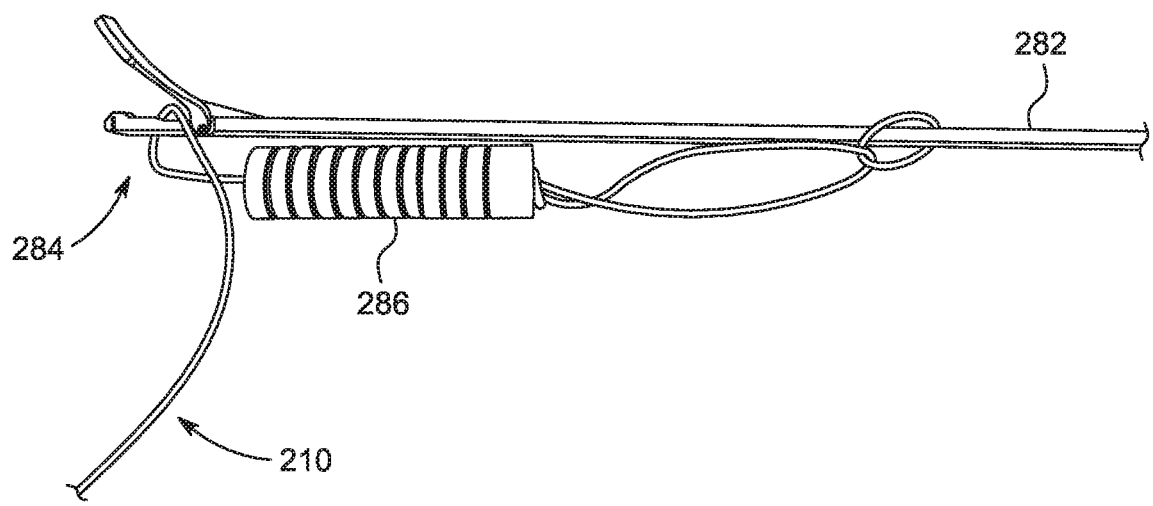
FIG. 6A is a side view of an embodiment of a self-cinching suture installation apparatus having a sheath disposed in a cartridge.
Figure 6B:
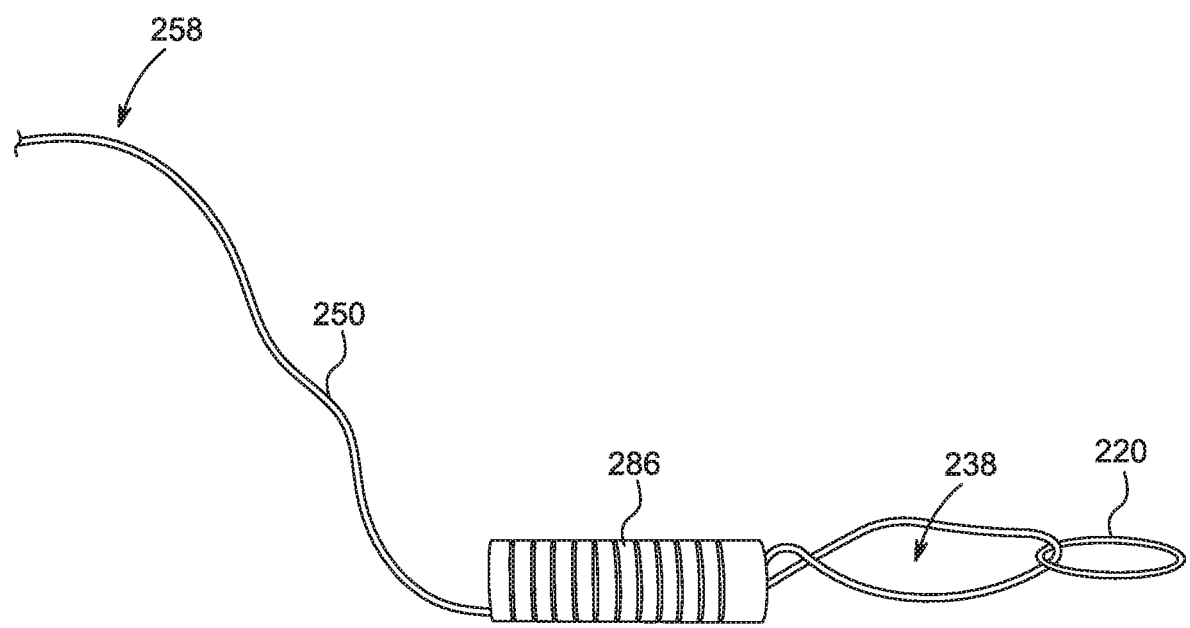
FIG. 6B is a side view of an embodiment of a cartridge housing a self-cinching suture.
Figure 7:
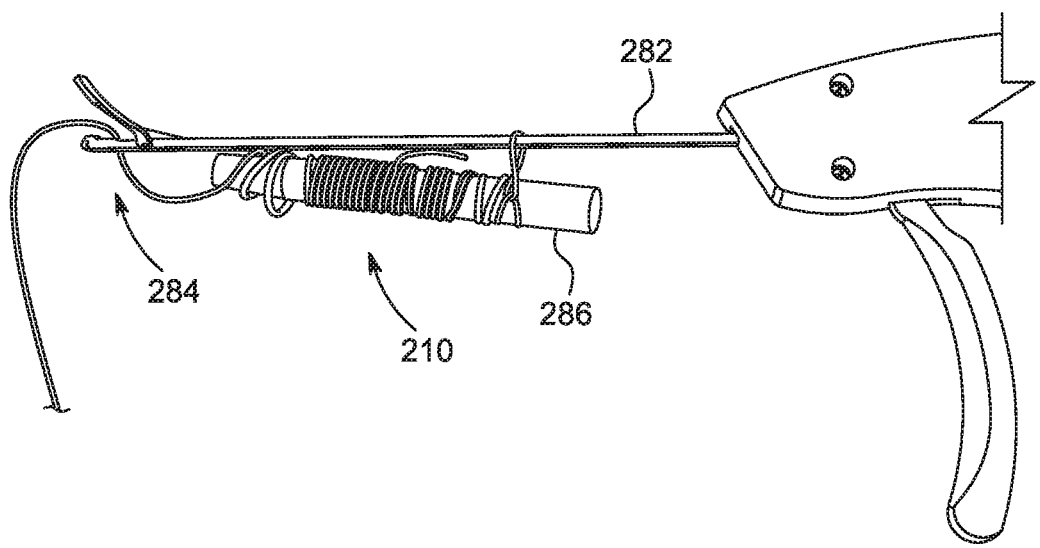
FIG. 7 is a side view of a self-cinching suture installation apparatus where a suture is disposed around a cartridge.

Now referring to FIGS. 6 and 7, a self-cinching suture installation apparatus 286 is provided. The self-cinching suture installation apparatus 280 may include readily available components such as a Ceterix® Novostitch® device. The self-cinching suture installation apparatus 280 may include a neck 282 and an insertion portion 284. As demonstrated in FIGS. 6A and 6B, one embodiment may include a cartridge 286 for retaining the sheathed device 210. The cartridge may be formed to include a hollow chamber operable to house at least a portion of the sheathed device 210 and permit the sheathed device 210 to be deployed as will be described hereafter. The cartridge 286 may retain the sheathed device 210 and may be loaded onto a self-cinching suture installation apparatus 280. FIG. 7 provides an alternative embodiment in which the cartridge 286 retains the sheathed device 210 on exterior portions of the cartridge 286. Other embodiments may be implemented as known to those of skill in the art.

Figure 8A:
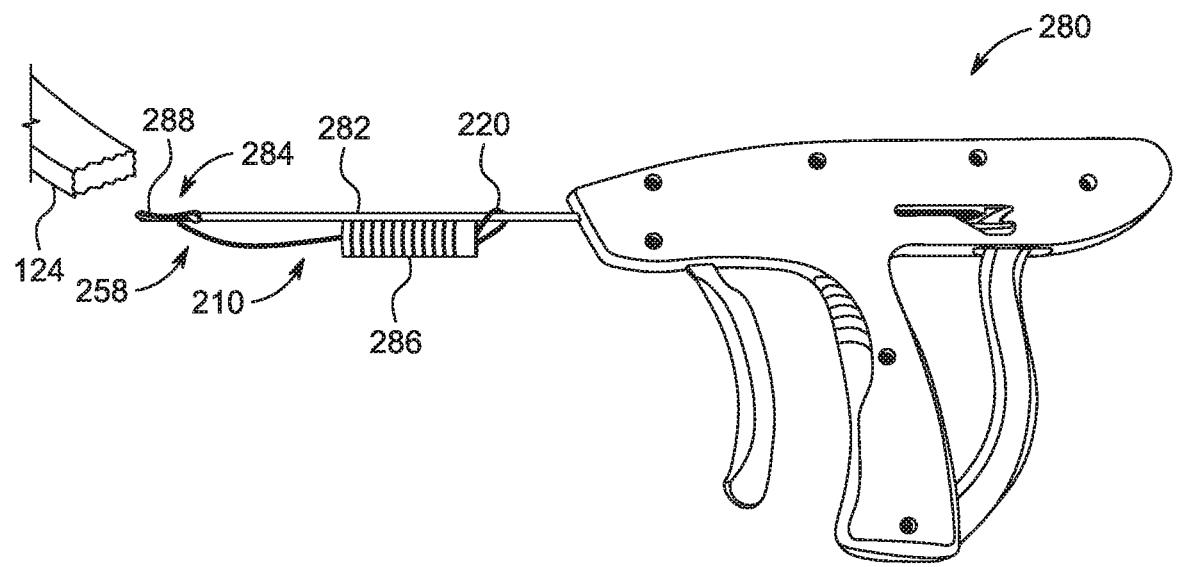
FIGS. 8A-8F illustrate an exemplary method of deploying a self-cinching suture construct apparatus using a self-cinching suture installation apparatus.
Figure 8B:
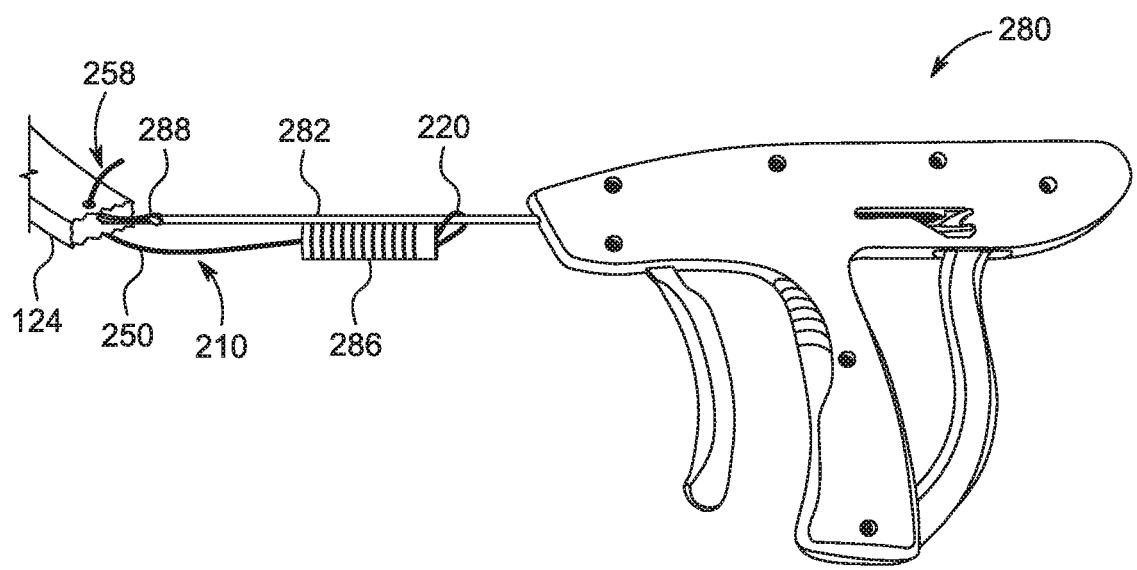

Referring to FIGS. 8A-8F, an exemplary deployment of a sheathed device 210 by a self-cinching suture installation apparatus 280 is provided. The sheathed device 210 may be installed in or on a cartridge 286 such that a portion of the sheathed device 210 is retained by the cartridge 286 and the continuous loop 220 is retained around the neck 282 of the self-cinching suture installation apparatus 280. In those embodiments in which the sheathed device implements an anchor 221, the anchor 221 may be contained in or on the cartridge 286. The distal end 258 of the sheath 250 may be retained by the insertion portion 284 of the self-cinching suture installation apparatus 280. When the self-cinching suture installation apparatus 280 is moved proximate the damaged tissue such as the meniscal root 124, the self-cinching suture installation apparatus 280 may be activated. The insertion portion 284 will either create a passage through the damaged tissue or it will pass through an existing passage formed through the damaged tissue. A retaining tip 288 of the self-cinching suture installation apparatus 280 will then retain the distal end 258 of the sheath 250 as the insertion portion retracts and releases the distal end 258, as seen in FIG. 8B.

Figure 8C:
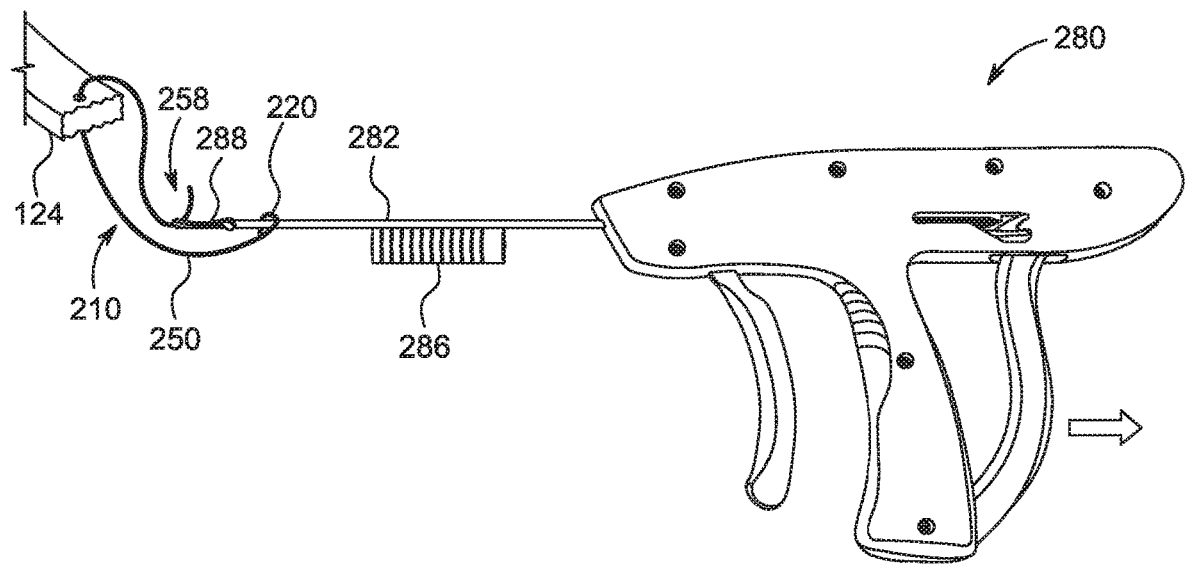

FIG. 8C depicts the self-cinching suture installation apparatus 280 being translated away from the damaged tissue. During this movement, the distal end 258 continues to be retained by the retaining tip 288 such that the sheathed device 210 advances through the passage in the damaged tissue. Likewise, as the self-cinching suture installation apparatus 280 is translated away from the damaged tissue, the continuous loop 220 translated axially down the neck 282 of the self-cinching suture installation apparatus 280 towards the retaining tip 288.

Figure 8D:
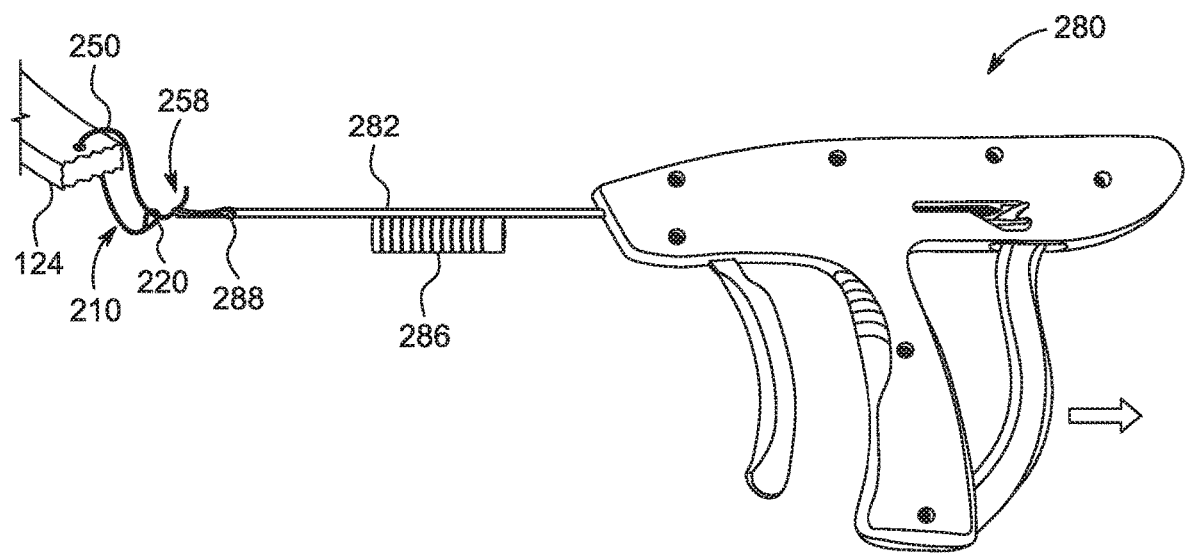
Figure 8E:
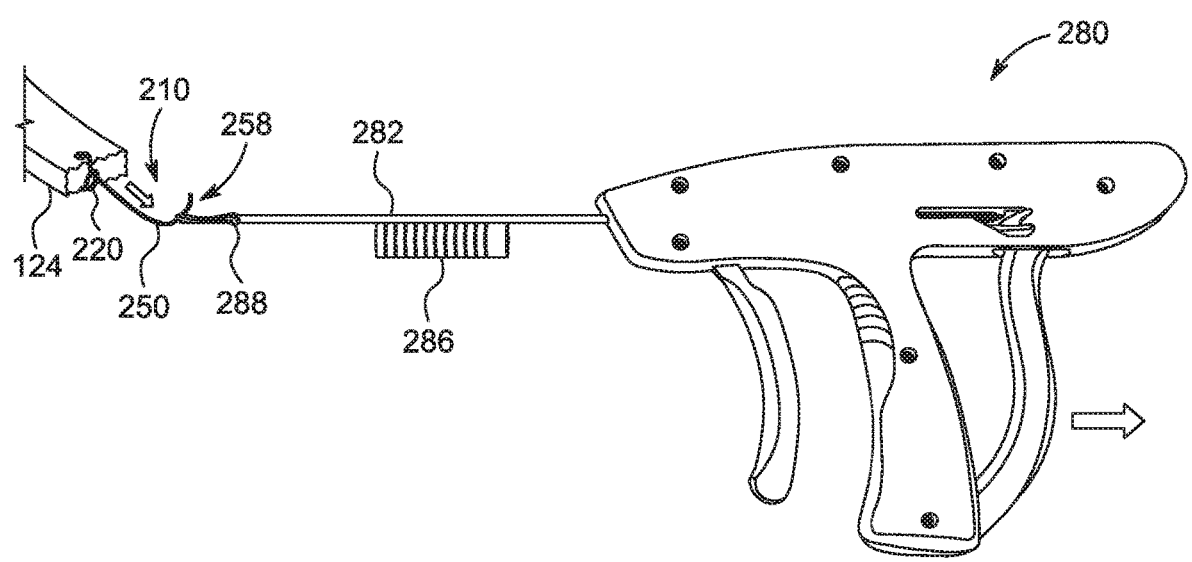

FIG. 8D demonstrates the continuous loop 220 axially sliding off the neck 282 and over the retaining tip 288 such that the distal end 258 of the sheath 250 and portions of the sheathed device 210 pass through the continuous loop 220. As the distal end 258 is retracted away from the damaged tissue, a girth hitch is formed on the damaged tissue as seen in FIG. 8E. In those embodiments where a continuous loop 220 is not implemented to secure the sheathed device 210 to the damaged tissue, an anchor 221 may be implemented. The anchor 221 may engage the damaged tissue as the sheathed device 210 is pulled through the damaged tissue and the anchor 221 contacts the damaged tissue. Various embodiments of the anchor 221 will be shown and discussed hereafter.

Figure 8F:
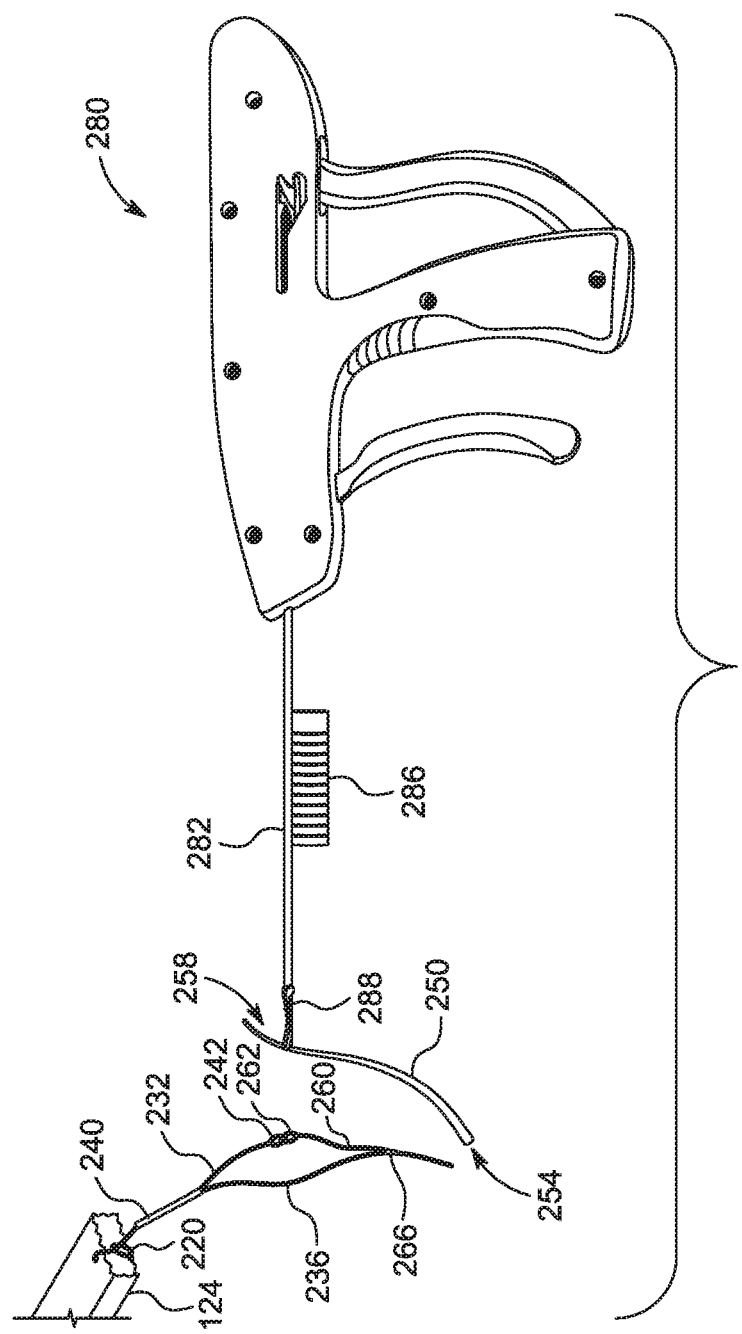

Referring to FIG. 8F, once the continuous loop 220 is securely fastened to the damaged tissue, the self-cinching suture installation apparatus 280 may be further translated away from the damaged tissue. As the tension increases along the sheathed device 210 a user may disengage the self-cinching suture installation apparatus 280 and release the distal end 258 of the sheath 250. A user may implement this method directly through a transosseous tunnel such that the sheathed device 210 is pulled by the self-cinching suture installation apparatus 280 directly through the transosseous tunnel. In some embodiments, as shown in FIG. 8F, as the tension increases, the distal end 258 of the sheath 250 may be retained by the self-cinching suture installation apparatus 280 and the sheath 250 may begin to slide off from the self-cinching suture member 232 and the remaining components of the sheathed device 210 such as the sacrificial suture 260. A user may implement this method when the neck 282 of the self-cinching suture installation apparatus 280 was inserted through the transosseous tunnel. Thus, as the self-cinching suture installation apparatus 280 is translated away from the damaged tissue, the sheathed device 210 is shuttled simultaneously through the transosseous tunnel.

Figure 9A:
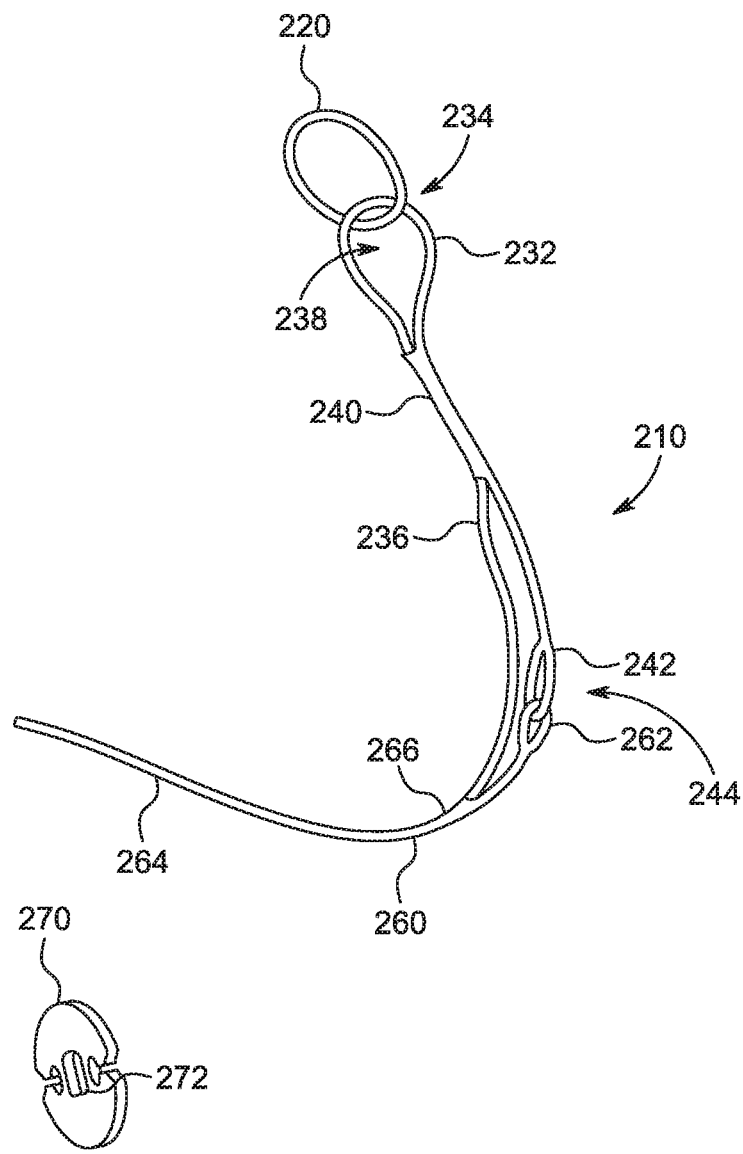
FIGS. 9A-9C illustrate an exemplary method of securing a self-cinching suture construct apparatus on a suture button.
Figure 9B:
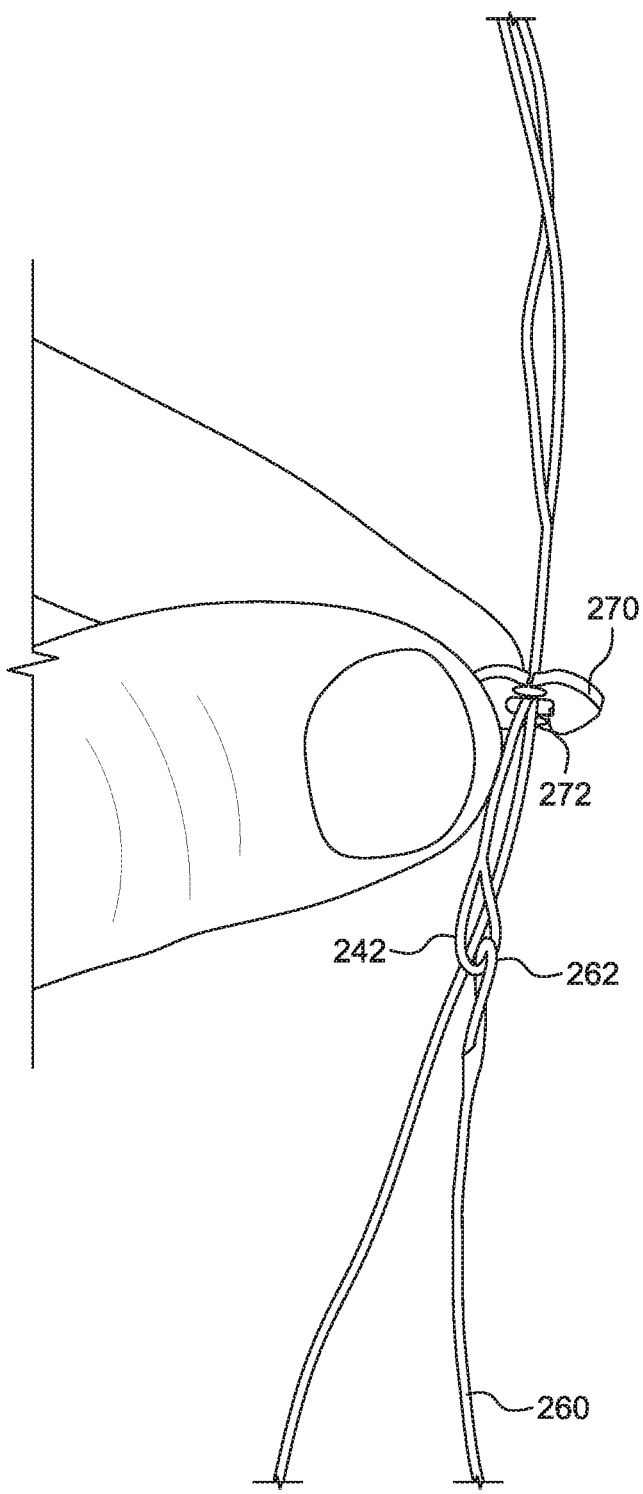
Figure 9C:
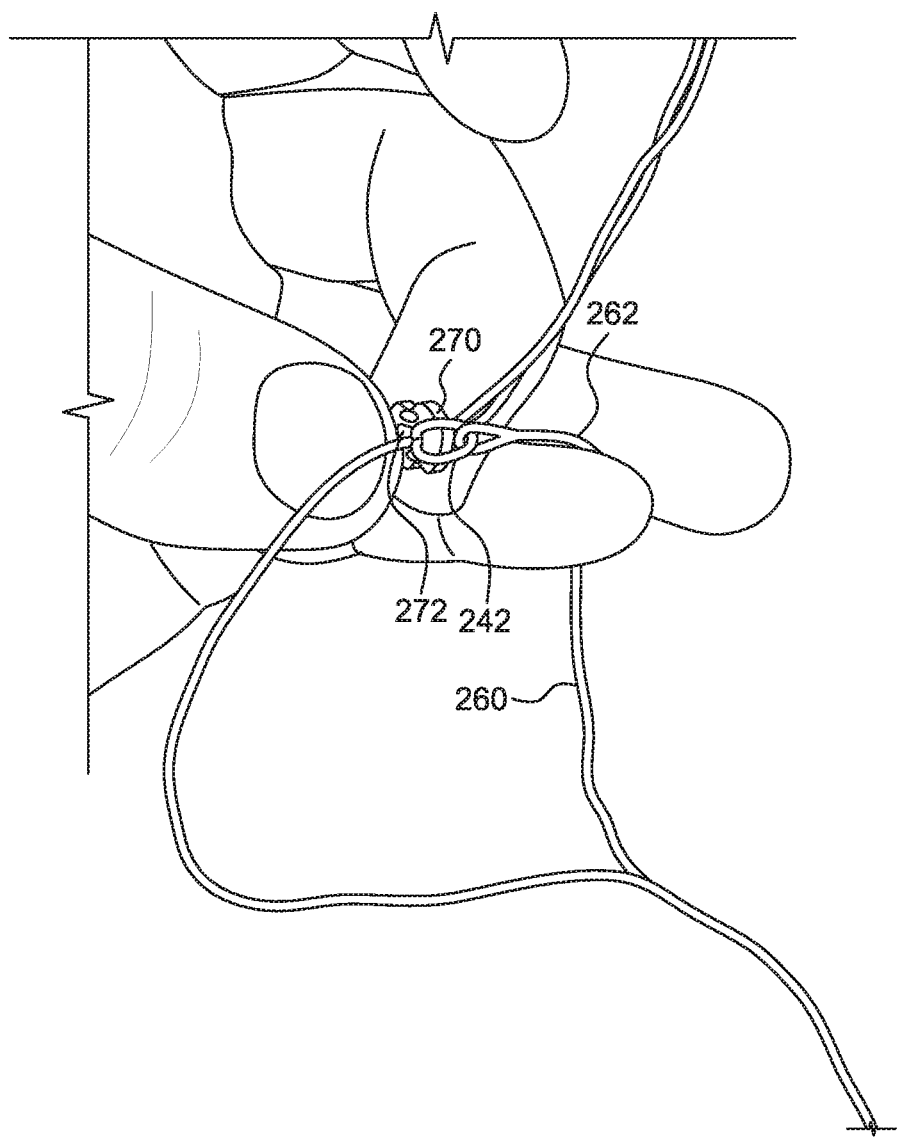

Now referring to FIGS. 9A-9C, a suture button 270 or suture anchor may be provided in combination with the sheathed device 210. After the sheathed device 210 has been installed on the damaged tissue and the sheath 250 has been removed from the self-cinching suture member 232 and the remaining components of the sheathed device 210 such as the sacrificial suture 260, the suture button 270 may be coupled to the self-cinching suture member 232. In some embodiments, the sacrificial suture strand 264 may be passed through a center passage 272 of the suture button 270. In those embodiments in which the self-cinching suture member free end 236 is retained by the sacrificial suture 260, as the suture button 270 is axially advanced along the sacrificial suture 260, the self-cinching suture member free end 236 also passes through the center passage 272. In some embodiments the self-cinching suture member free end 236 is retained by the sacrificial suture 260 in a sacrificial suture sleeve 268 formed on the sacrificial suture strand 264. In other embodiments, the self-cinching suture member free end 236 may be coupled to the sacrificial suture 260 by an adhesive or be woven into the sacrificial suture strand 264.

FIG. 9B demonstrates an exemplary embodiment in which the suture button 270 and the center passage 272 are advanced along the self-cinching suture member 232. Once the suture button 270 has advance passed the self-cinching suture fixed loop 242, a user may use the self-cinching suture fixed loop 242 to secure the suture button 270 to the self-cinching suture member 232. As shown in FIG. 9C, the self-cinching suture fixed loop 242 may be passed back over a longitudinal end of the suture button 270 such that the self-cinching suture fixed loop 242 forms a girth hitch over the suture button 270. A user may use the sacrificial suture 260 in order to better maneuver the self-cinching suture fixed loop 242 over the longitudinal end of the suture button 272. After the self-cinching suture fixed loop 242 is installed on the suture button 272, the sacrificial suture 260 may be cut from the self-cinching suture fixed loop 242. As the sacrificial suture 260 is removed from the sheathed device 210, the self-cinching suture member free end 236 may be removed or come loose from the sacrificial suture 260.

Once the suture button 270 is secured to the self-cinching suture fixed loop 242, a user may then tension the self-cinching suture member 232 by pulling the self-cinching suture member free end 236 and advancing the self-cinching suture member free end 236 through the self-cinching suture sleeve 240. As the self-cinching suture member free end 236 is advanced through the self-cinching suture sleeve 240, the suture button 270 is pulled towards the transosseous tunnel 138 until the suture button is reduced on the surface of the bone, firmly rests on the bone, and is substantially flush with the bone. A user may apply tension to the self-cinching suture free end 236 until the appropriate tension is applied across the self-cinching suture member 232 and the damaged tissue is reduced to the correct anatomical position. The excess self-cinching suture member free end 236 may be cut at or near the center passage 272.

Thus, a user may engage and retain portions of tissue in a desired position using the sheathed device 210. As the sheathed device 210 is operable to be installed through the damaged tissue such that the anchor 221 (in those embodiments implementing an anchor 221) is the last component to pass towards the damaged tissue, many various embodiments of the anchor 221 may be implemented to improve surgical outcomes and healing by preventing tear through or failure of the sheathed device 210 after installation.

Figure 10:
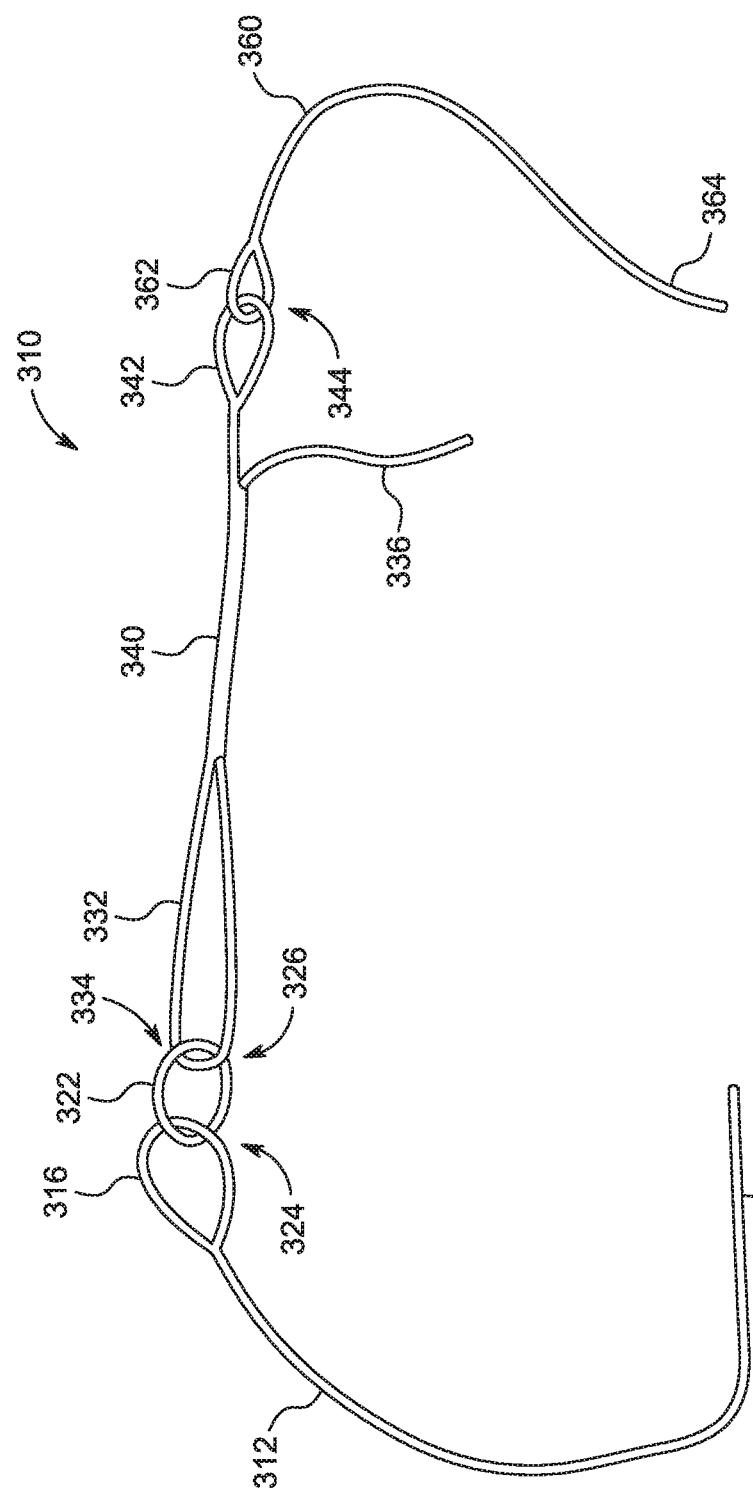
FIG. 10 is a perspective view of an embodiment of a self-cinching suture construct apparatus implementing two shuttling sutures.

Another embodiment of the device 10 includes the double shuttling suture device 310. Referring to FIG. 10, the double shuttling suture device 310 includes a continuous-loop shuttling suture 312 forming a leading continuous-loop shuttling suture free end 314. Continuous-loop shuttling suture 312 includes a continuous-loop shuttling suture fixed loop 316 at its trailing end opposite the leading continuous-loop shuttling suture free end 314. Leading continuous-loop shuttling suture free end 314 on shuttling suture 312 is positioned for initial insertion into the injured tissue for beginning a suture attachment procedure.

The embodiment of a double shuttling suture device 310 shown in FIG. 10 is not drawn to scale, and the relative lengths, shapes and diameters of the various suture construct features may vary considerable based on the desired application. This is likewise applicable to many of the FIGS of the application in order to demonstrate many of the features of the devices.

Next to the continuous-loop shuttling suture 312, a ring-shaped continuous loop 322 is attached to the continuous-loop shuttling suture fixed loop 316. Continuous loop 322 forms a continuous ring passing through the opening formed by the shuttling suture fixed loop 316. Continuous loop 322 includes a continuous loop leading edge 324 and a continuous loop trailing edge 326. Continuous loop leading edge 324 provides the engagement location between continuous loop 322 and shuttling suture fixed loop 316. Continuous loop 322 includes any suitable suture material known in the art. Continuous loop 322 may be formed by splicing or connecting tag ends of a strand of suture material together. Similarly, continuous-loop shuttling suture fixed loop 316 may be formed by splicing or connecting a tag end of continuous-loop shuttling suture 312 back onto itself to form a fixed loop. Alternatively, continuous loop 322 or continuous-loop shuttling suture fixed loop 316 may be integrally formed on each respective suture member in a molding process.

A third, self-cinching suture member 332 is disposed on the double shuttling suture device joining continuous loop 322. The self-cinching suture member 332, or knotless repair suture 332, includes a self-cinching suture leading end 34 positioned on the forward end toward the continuous loop 322. The self-cinching suture leading end 334 passes through the ring-shaped opening formed by continuous loop 322. Self-cinching suture member 332 is configured to pass through a transosseous tunnel 138 in a patient's bone during a meniscal root tear repair procedure in some embodiments.

Referring further to FIG. 10, a self-cinching suture sleeve 340 is disposed on the self-cinching suture member 332. In some embodiments, self-cinching suture member 332 is constructed of a suture material having an annular cross-sectional profile, forming an elongated tube. Such suture material may include braided or non-braided suture material. In some embodiments, self-cinching suture sleeve 340 is defined within the interior hollow body of the suture material.

For example, a self-cinching suture member free end 36 may be passed through a self-cinching suture sleeve segment 340 of the self-cinching suture member body, as shown in FIG. 10. The segment of the suture body surrounding the passed-through portion forms a self-cinching suture sleeve 340 around the suture strand of the self-cinching suture member free end 336.

Thus, a portion of the suture strand between self-cinching suture member free end 336 and the self-cinching suture leading end 334 may slide through self-cinching suture sleeve 340. As tension is applied to the suture member, the self-cinching suture sleeve 340 may tighten around the suture strand passing through self-cinching suture sleeve 340, thereby securing or locking the suture strand in place relative to the self-cinching suture sleeve. Self-cinching suture sleeve 340 provides a clamping effect against the strand of suture material passing through the self-cinching suture sleeve. The clamping effect prevents the strand from inadvertently loosening during use. More specifically, during use, when self-cinching suture member 332 is pulled tight, self-cinching suture sleeve 340 restricts axial translation of self-cinching suture member free end 336. As such, the suture member may be referred to as a "self-cinching" or "knotless" suture construct.

Referring further to FIG. 10, another feature of self-cinching suture member 332 includes a retaining structure such as a self-cinching suture fixed loop 342 formed at the self-cinching suture trailing end 344. During a surgical procedure, a suture button 370 or suture anchor may be secured to double shuttling suture device 310 at the self-cinching suture fixed loop 342. The application of tension to self-cinching suture member free end 336 causes the self-cinching suture member 332 to slide through continuous loop 322 and to be generally drawn back toward the continuous loop 322. This motion effectively forms an adjustable loop 338, which closes as tension is applied.

The double shuttling suture device 310 may further comprise a self-cinching member shuttling suture 360 forming a self-cinching member shuttling suture free end 364. Self-cinching member shuttling suture 360 includes a shuttling suture fixed loop 362 at an end opposite the self-cinching member shuttling suture free end 364, the shuttling suture fixed loop 362 attached to the self-cinching suture fixed loop 342. Alternatively, self-cinching suture fixed loop 342 or shuttling suture fixed loop 362 may be integrally formed on each respective suture member in a molding process. The self-cinching member shuttling suture free end 364 on self-cinching member shuttling suture 360 may likewise be positioned for initial insertion into the injured tissue for beginning the suture attachment procedure.

Figure 11A:
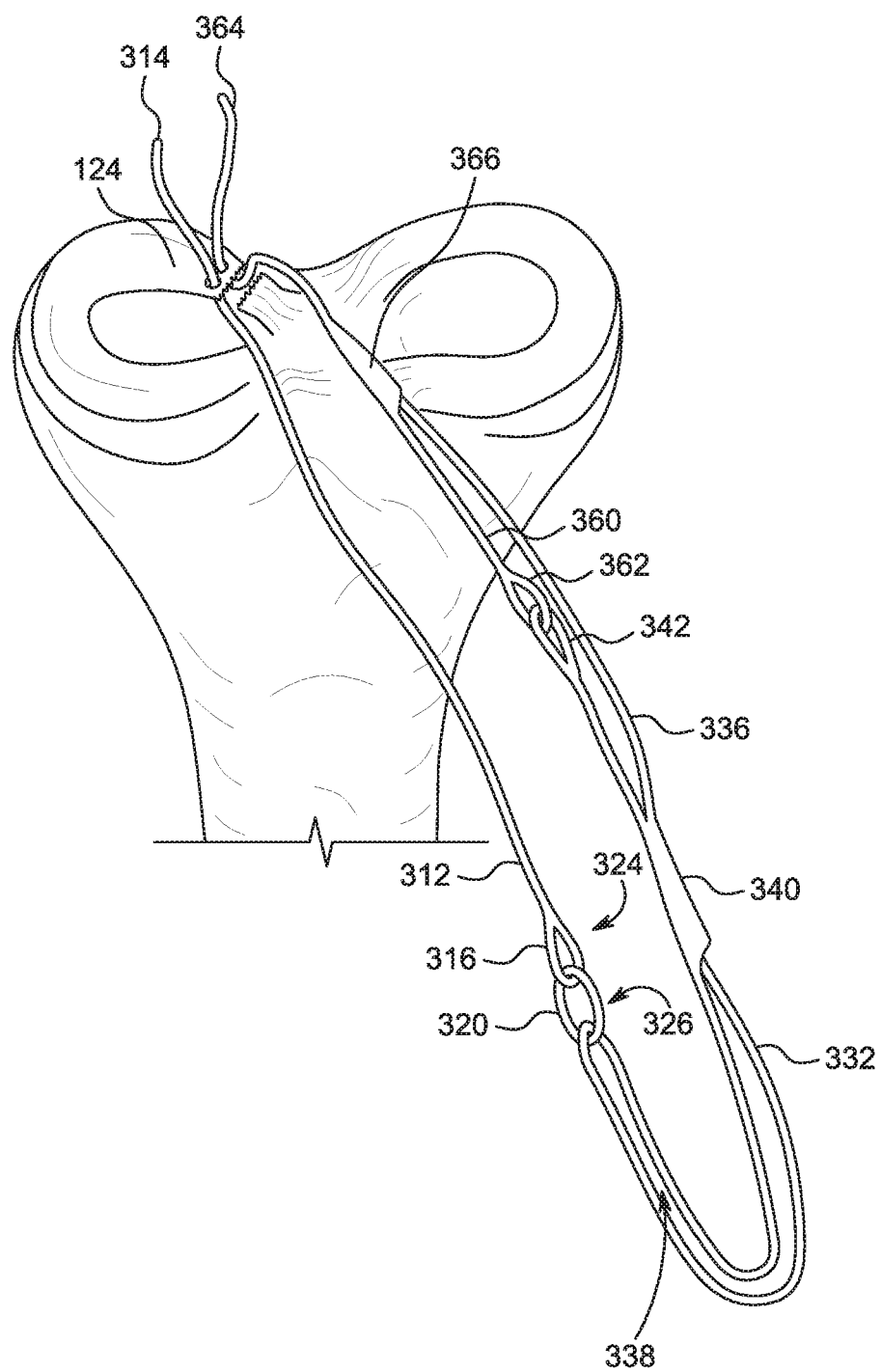
FIG. 11A-11E illustrate an exemplary method of using a self-cinching suture construct apparatus implementing two shuttling sutures.

An example of a double shuttling suture device 310 configured for meniscus root tear repair is shown in FIGS. 11A-11E. The double shuttling suture device 310 may include four main components: a continuous-loop shuttling suture 312, a continuous loop 322, a self-cinching suture member 332, and a self-cinching member shuttling suture 360. Referring to FIG. 11A, the leading shuttling suture free end 314 is inserted through the damaged tissue of a meniscus root 124. The leading continuous-loop shuttling suture free end 314 may be inserted in the torn meniscal root 124 using any suitable instrument for passing a suture through tissue. Likewise, the self-cinching member shuttling suture free end 364 may be inserted in the torn meniscal root 124 using any suitable instrument for passing a suture through tissue. Thus, both free ends of the shuttling sutures are inserted in the torn meniscal root 124. As the free ends 314, 364 are passed through the torn meniscal root tissue, passage holes 134a, 134b are formed, creating openings in the soft tissue of the injured tissue through which the suture material of the shuttling suture 312 may slide.

Figure 11B:
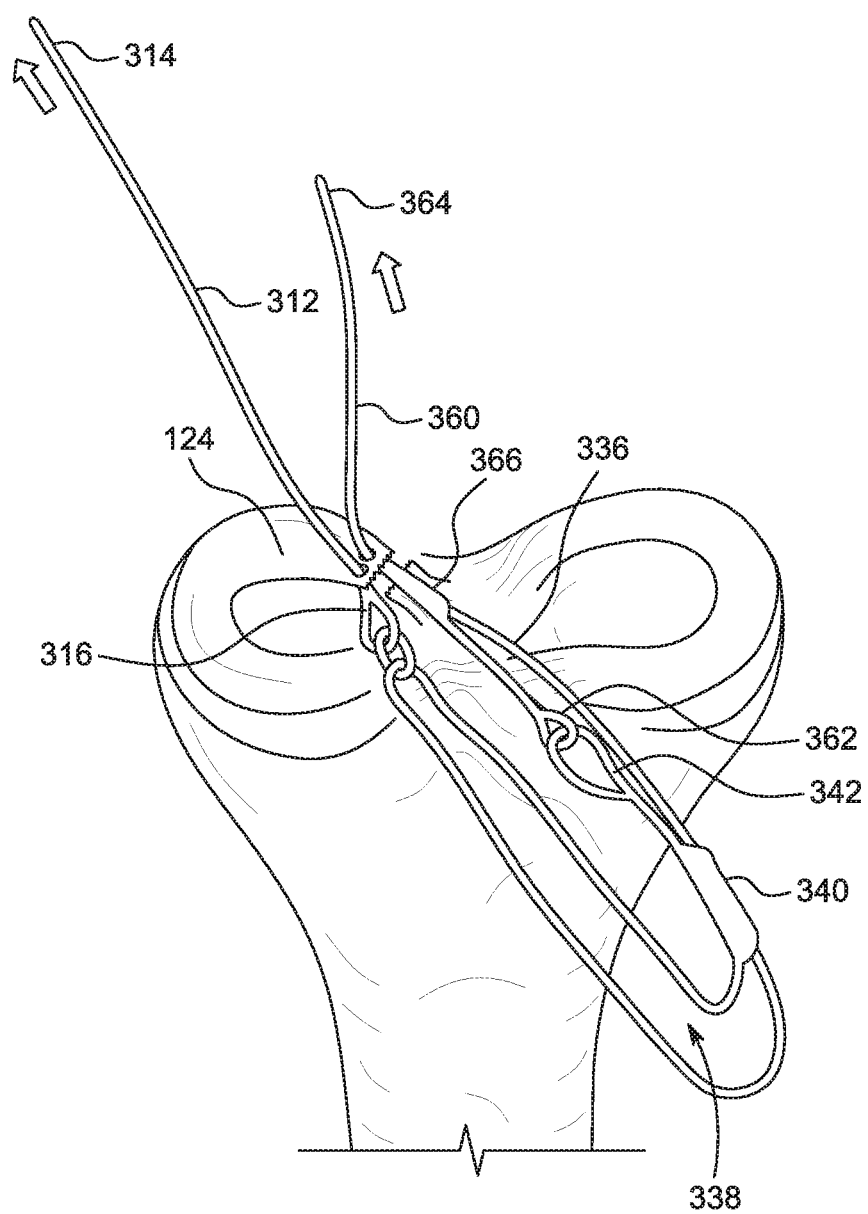

Referring now to FIG. 11B, the free ends 314, 364 may be advanced through the damaged tissue. As the leading continuous-loop shuttling suture free end 314 is advanced through the tissue, the continuous loop 322 may be positioned proximate and pulled through the damaged tissue, as demonstrated in FIG. 11C.

Figure 11C:
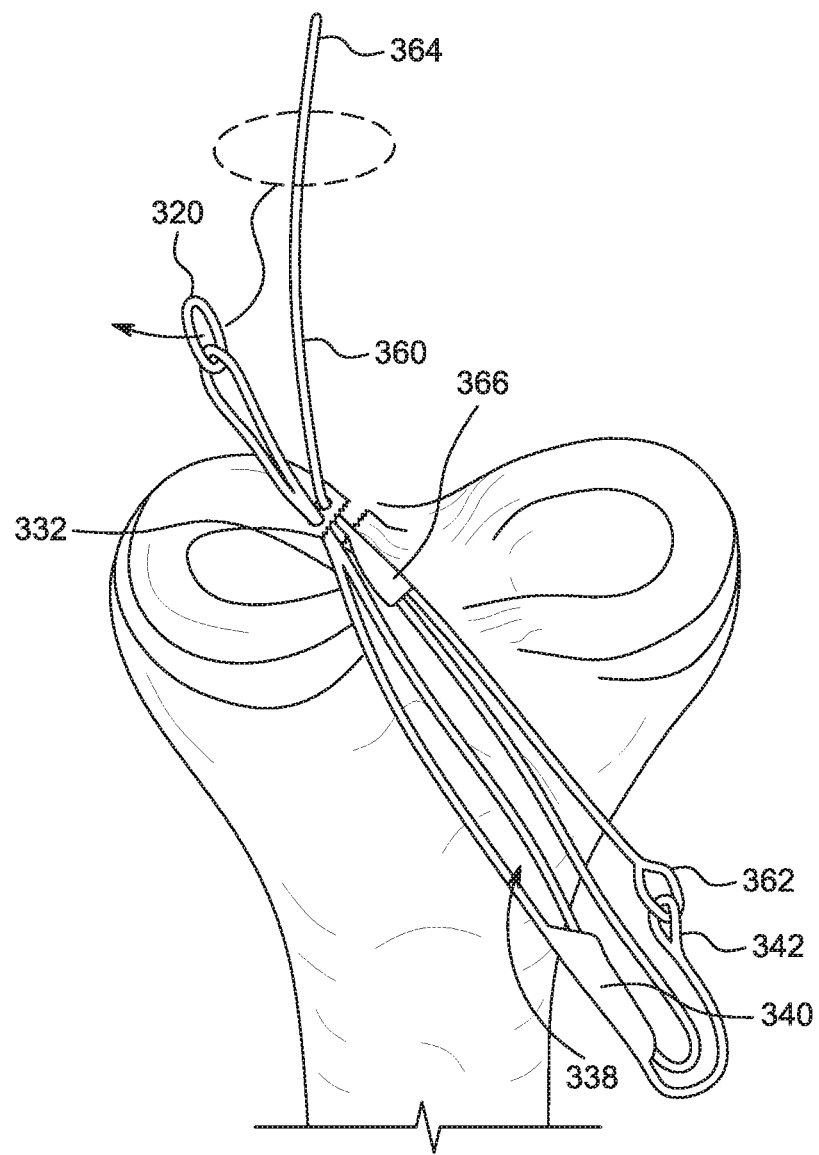

FIG. 11C further demonstrates that once the continuous-loop shuttling suture 312 has pulled the continuous loop 322 through the damaged tissue, the continuous-loop shuttling suture 312 may be removed. The self-cinching member shuttling suture free end 364 may be inserted in and pulled through the continuous loop 322. When this occurs, the self-cinching member shuttling suture free end 364 is pulled and tensioned and a double hitch is formed on the tissue with two planes of tissue being captured, which provides additional fixation to the damaged tissue by the continuous loop 322, thus allowing for greater engagement with the damaged tissue.

In alternative embodiments in which the user implements an anchor 321 rather than the continuous loop 320, an alternative method of securement to the damaged tissue may be implemented, as one of skill in the art would recognize.

Figure 11D:
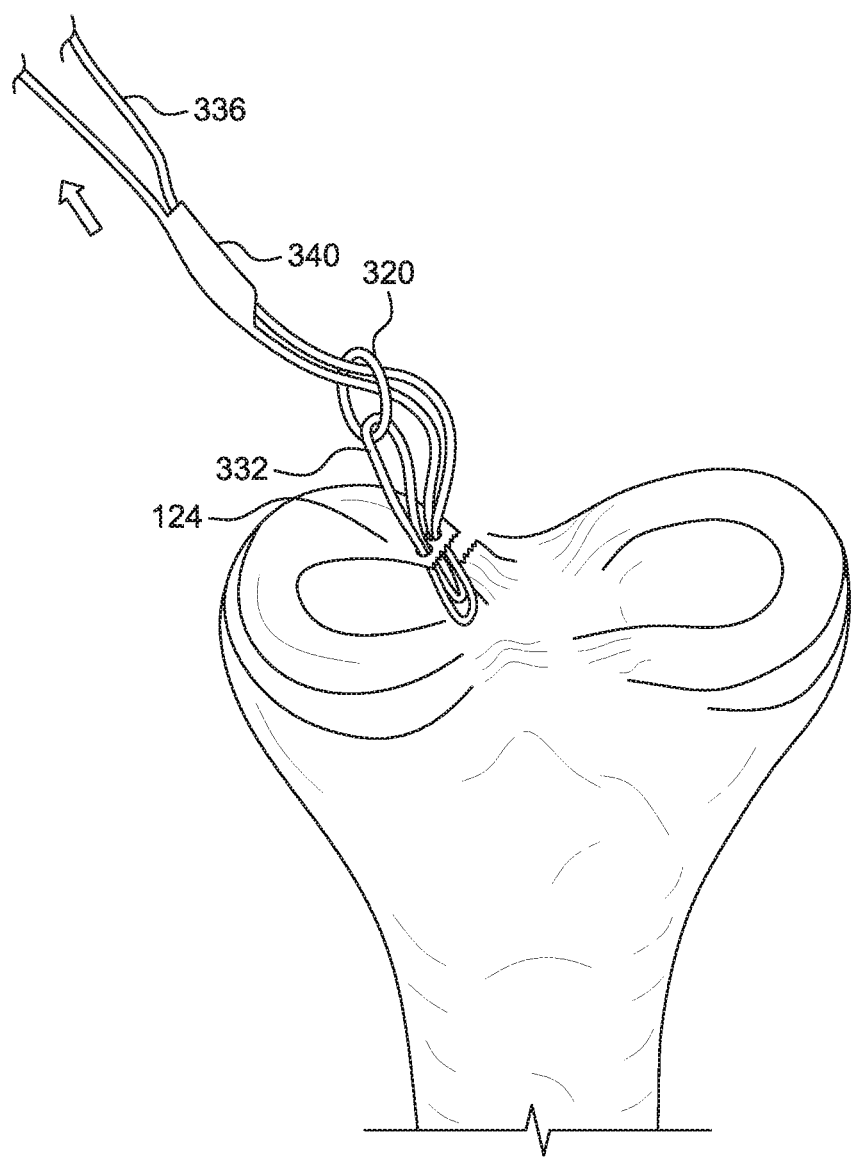
Figure 11E:
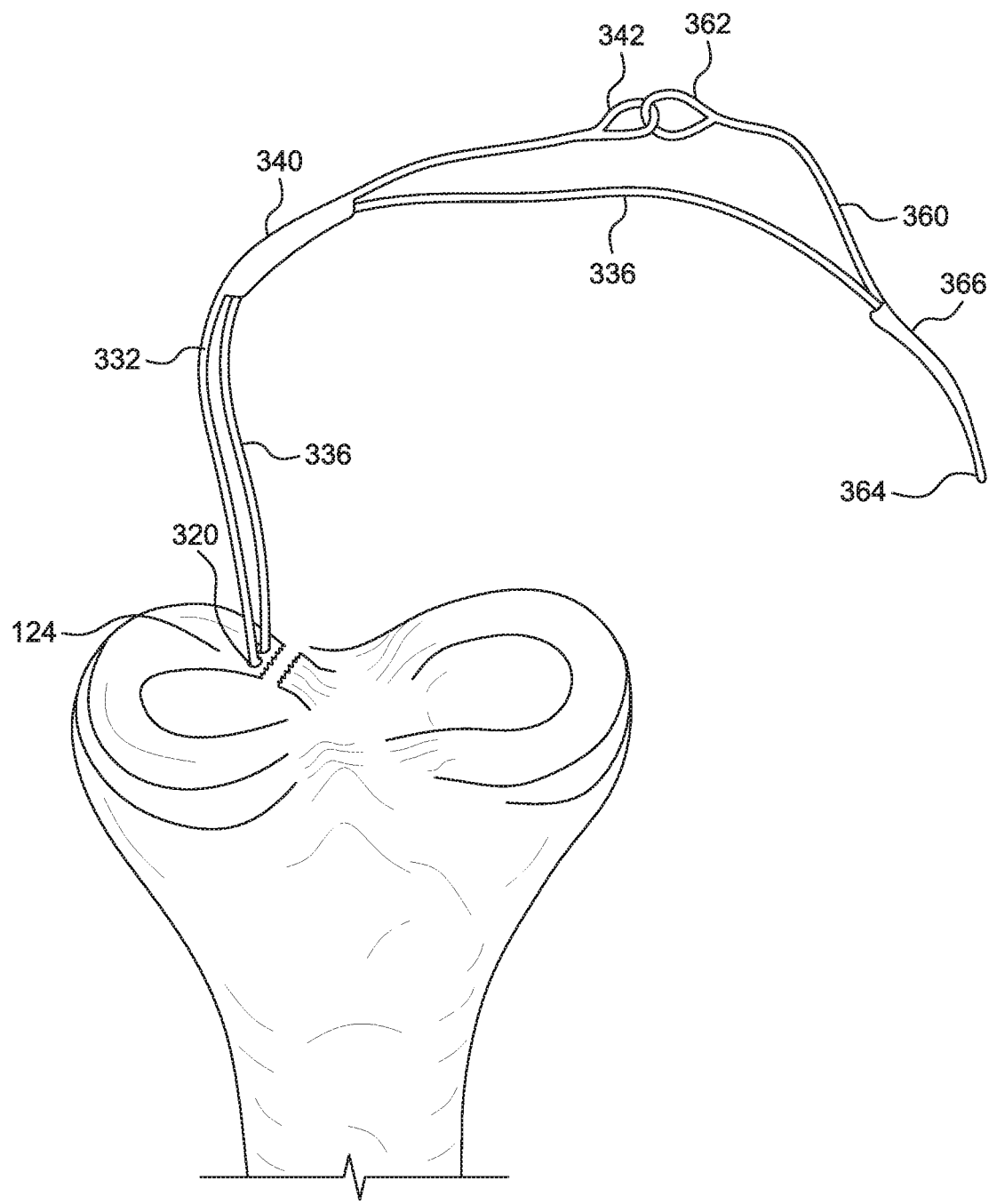
Figure 12:
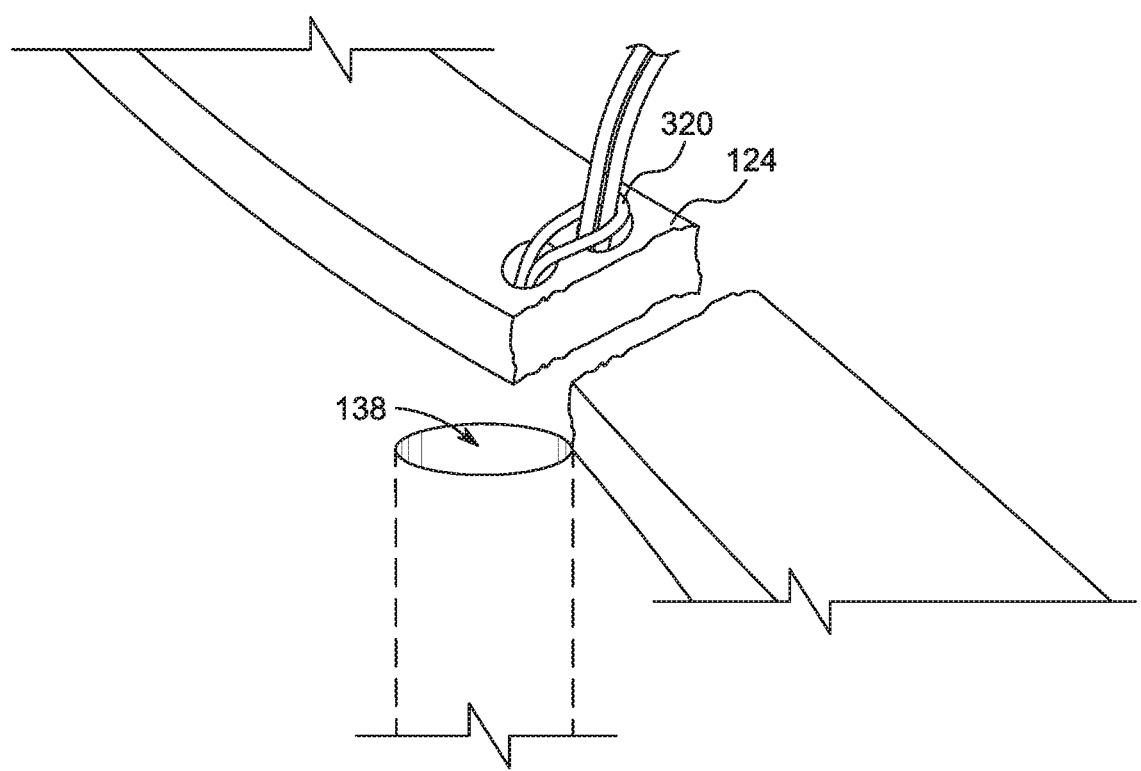
FIG. 12 is a perspective view of an exemplary interface between damaged tissue and the implementing a self-cinching suture construct apparatus.

Now referring to FIGS. 11D, 11E, and 12, the double shuttling suture device 310 may be secured to the damaged tissue. The remainder of the method for reducing the damaged tissue to the correct anatomical position via a suture button 370 and a transosseous tunnel 138 is similar to those previously described and disclosed in FIGS. 5 and 9. Thus, the double shuttling suture device 310 may be implemented in repairing damaged tissue including meniscal root repairs. Furthermore, the various components as described in connection with the sheathed device 210 may likewise be implemented with the double shuttling suture device 310, including a sheath and a shuttling suture sleeve 268 as one of skill in the art would recognize. In addition, the various components as discussed with regard to the double shuttling suture device 310 may also be used in connection with the sheathed device 210 as one of skill in the art would recognize.

As previously discussed, the various devices and embodiments may implement an anchor 21. Although this application discusses the use of the anchor 21 specifically with the meniscus, these same embodiments may be implemented on a variety of tissues to provide securement of and interface with tissues, both healthy and damaged, as would be recognized by one of skill in the art.

Referring to FIG. 12, a user may secure a torn meniscal root 124 via a double hitch, where the suture material and the double hitch passes through two planes of the meniscal root 124. For example, a continuous loop 20 may be implemented to form the double hitch. When a fixed loop is implemented, the fixed loop may include a double fixed loop or a fixed loop having the adjoining component passing through the fixed loop material. Alternatively, disk anchors may provide a surface that may rest flush with the damaged tissue and prevent tear through of the fixation and the damaged tissue.

A variety of disk anchors may be implemented including a disk 412 with a loop 414 or multiple loops. For example, a loop 414 may pass through a portion of the disk 412 and form an anchor 21. The loop 414 may include a single loop, a double loop, or any other loop known to one of skill in the art. Various embodiments using a disc are disclosed in FIGS. 14A-14L. The disk may be implemented using a variety of materials, including soft rubber, HMWPE, synthetic material, and a collagen scaffold. In some embodiments, the anchor 21 may include a variety of loops, some of which are disclosed in FIGS. 15A-15D.

Figure 13A:
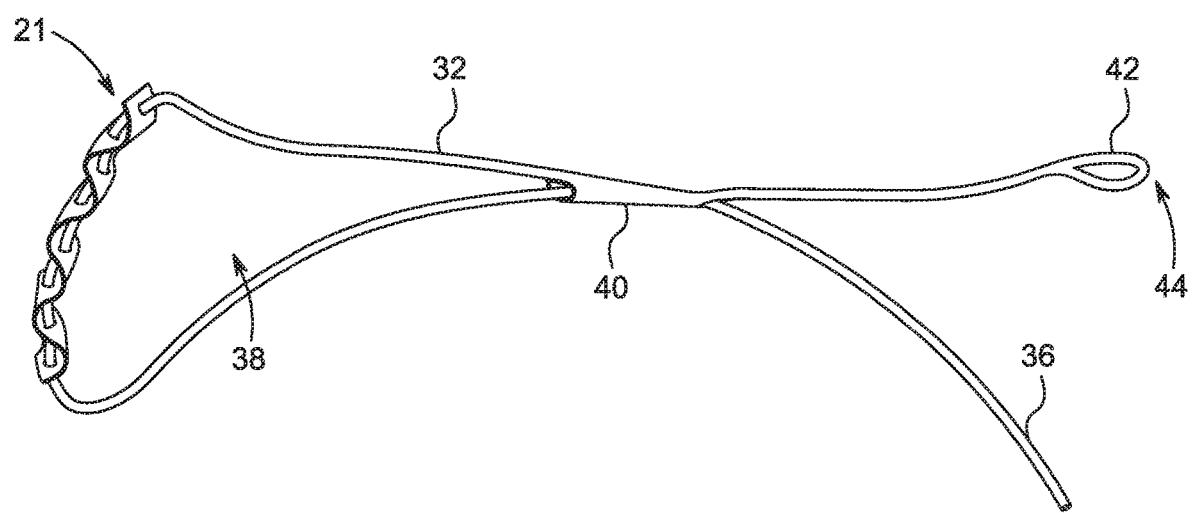
FIG. 13A is a perspective view of an exemplary embodiment of an anchor disposed on a self-cinching suture device.
Figure 13B:
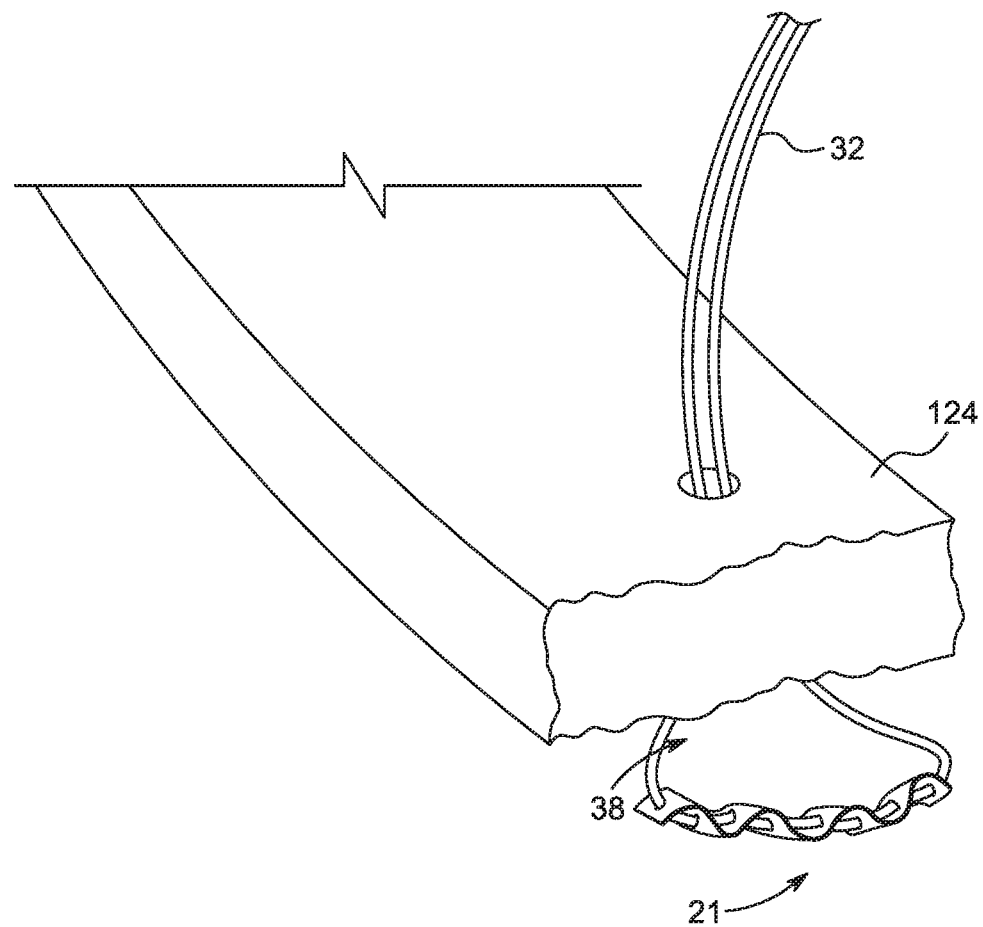
FIGS. 13B-13D are perspective views of an exemplary soft anchor used to secure damaged tissue.
Figure 13C:
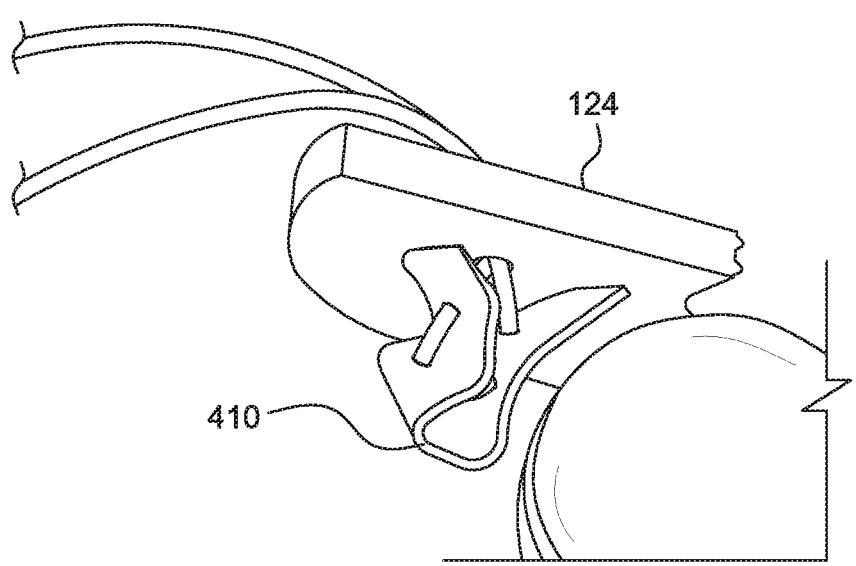
Figure 13D:
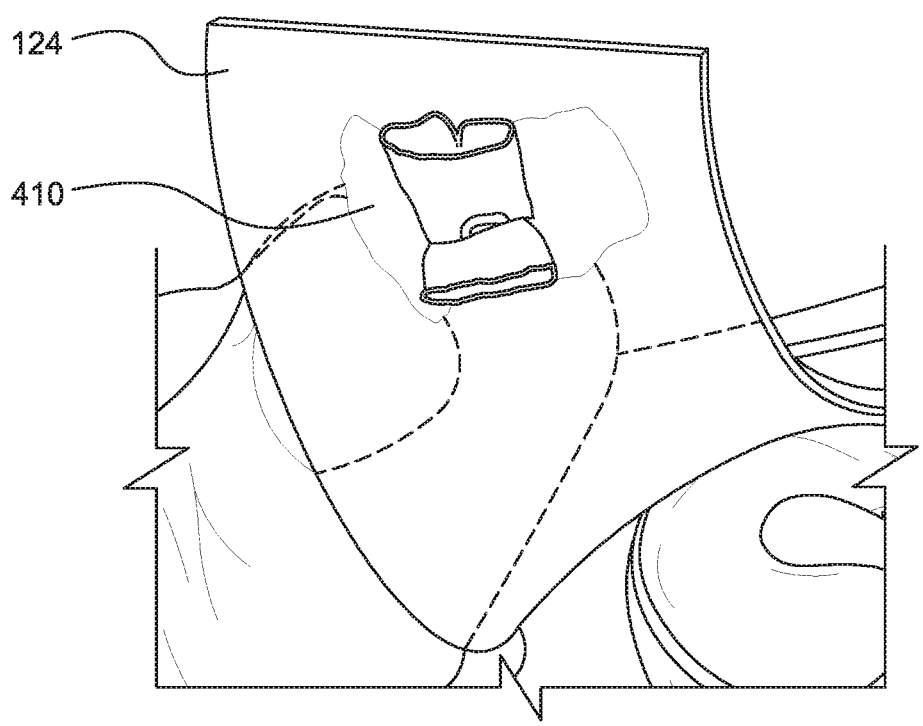
Figure 14A:
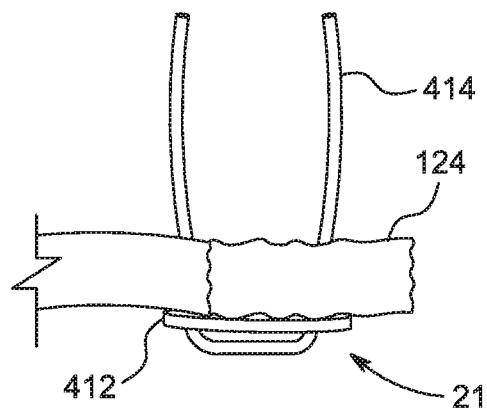
FIGS. 14A-14L are perspective views of an exemplary disk anchor used to secure damaged tissue.
Figure 14B:
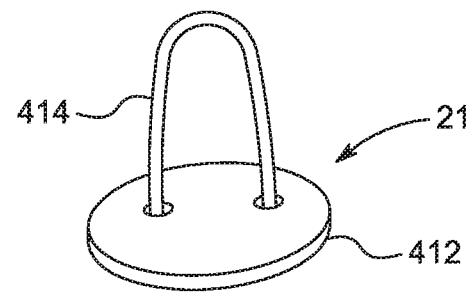
Figure 14C:
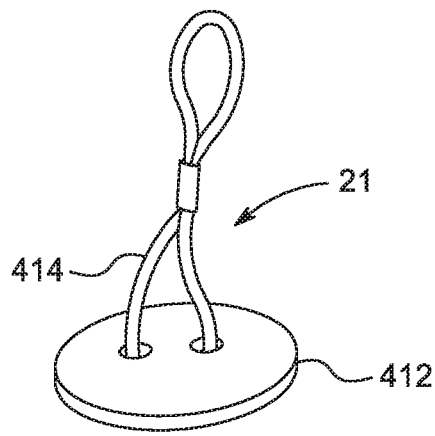
Figure 14D:
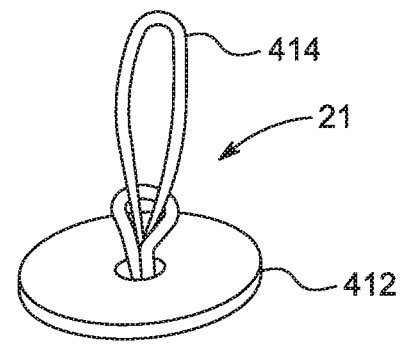
Figure 14E:
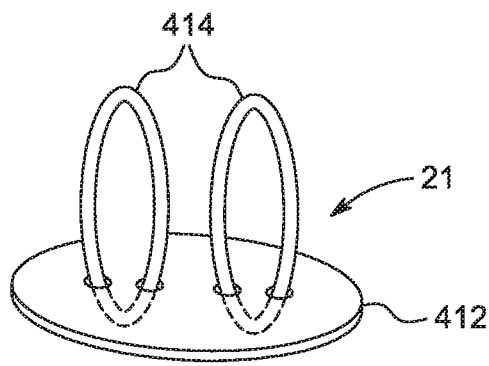
Figure 14F:
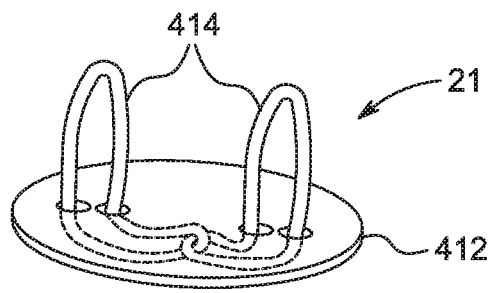
Figure 14G:
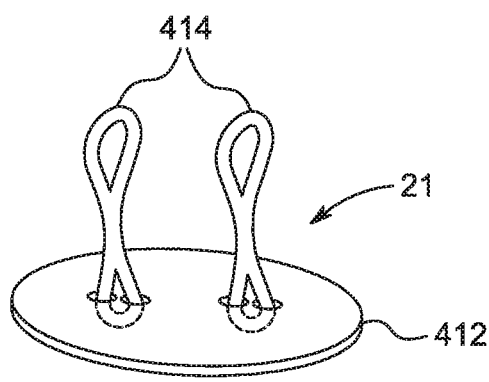
Figure 14H:
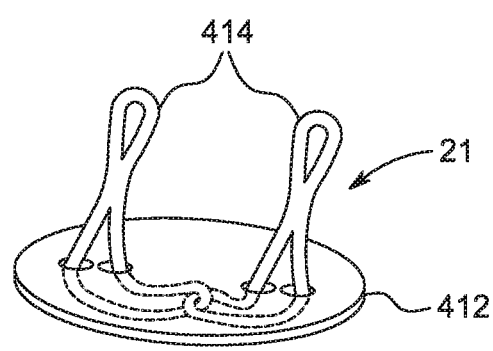
Figure 14I:
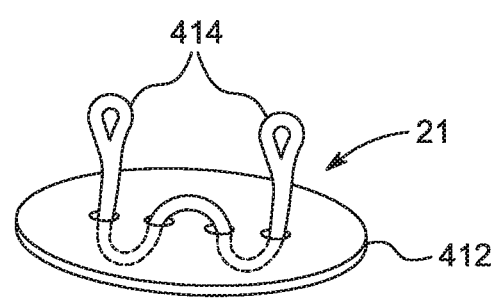
Figure 14J:
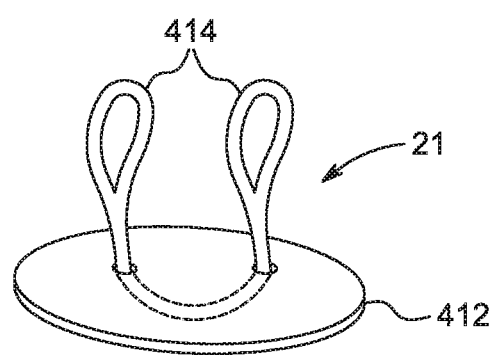
Figure 14K:
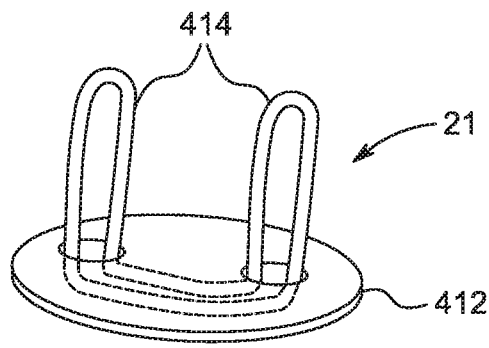
Figure 14L:
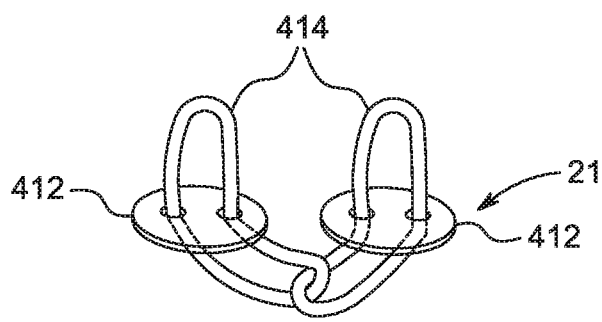
Figure 15A:
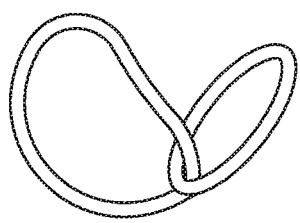
FIGS. 15A-15D are perspective views of various embodiments of anchors used to secure damaged tissue.
Figure 15B:
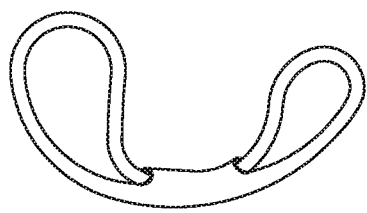
Figure 15C:
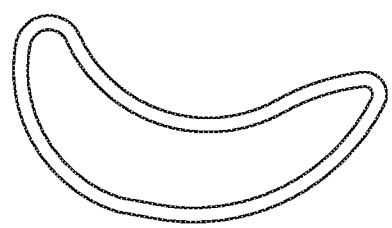
Figure 15D:
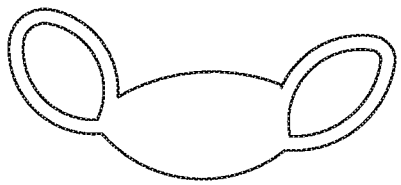

In those embodiments in which the anchor 21 does not implement a fixed loop, the anchor 20 may include a soft anchor 410. The soft anchor 410 may include a material that is transversely bunched when deployed. For example, with reference to FIGS. 13A-13C, a section of suture may pass through the superior and inferior surfaces of the soft anchor 410. The soft anchor 410 may be operable to prevent rubbing and friction between the damaged tissue and the suture material when the suture material is being pulled through and adjusted in the damaged tissue. FIG. 13B demonstrates an exemplary embodiment in which a soft anchor 410 is implemented. The suture may pass through the soft anchor 410 such that the suture is woven into the soft anchor 410. When both ends of the suture and passed through a single passage in a tissue, the soft anchor 410 will contact the exterior surface of the tissue and will begin to bunch, thus creating a surface area that prevents the soft anchor 410 and the portion of the suture in contact with the soft anchor 410 from passing through the tissue, as seen in FIG. 13C.

In another embodiment, the soft anchor 410 may include a material that is axially bunched when deployed. For example, the soft anchor 410 may comprise a sleeve that surrounds a portion of the suture. Thus, as the suture is pulled through the damaged tissue, the soft anchor 410 bunches and prevents the soft anchor and the remaining suture material from passing through the damaged tissue, thus anchoring the suture to the damaged tissue.

FIGS. 14A-14L provide exemplary embodiments of various anchors 21. The anchors 21 may comprise a disk or multiple disks. Further, the disk may have a securing portion coupled to or passing through the disk. In some embodiments, there may be multiple securing portions operable to receive a suture. The disk may provide a surface that receives a normal force of the tissue when a force is applied to the disk, such as occurs during tensioning. The disk may prevent the anchor from passing through the tissue.

FIGS. 15A-15D provide various embodiments of anchors 21. Likewise, the embodiments shown in these figures may be implements to form girth hitches when used in a manner similar as described with regards to the continuous loop 20.

Figure 17A:
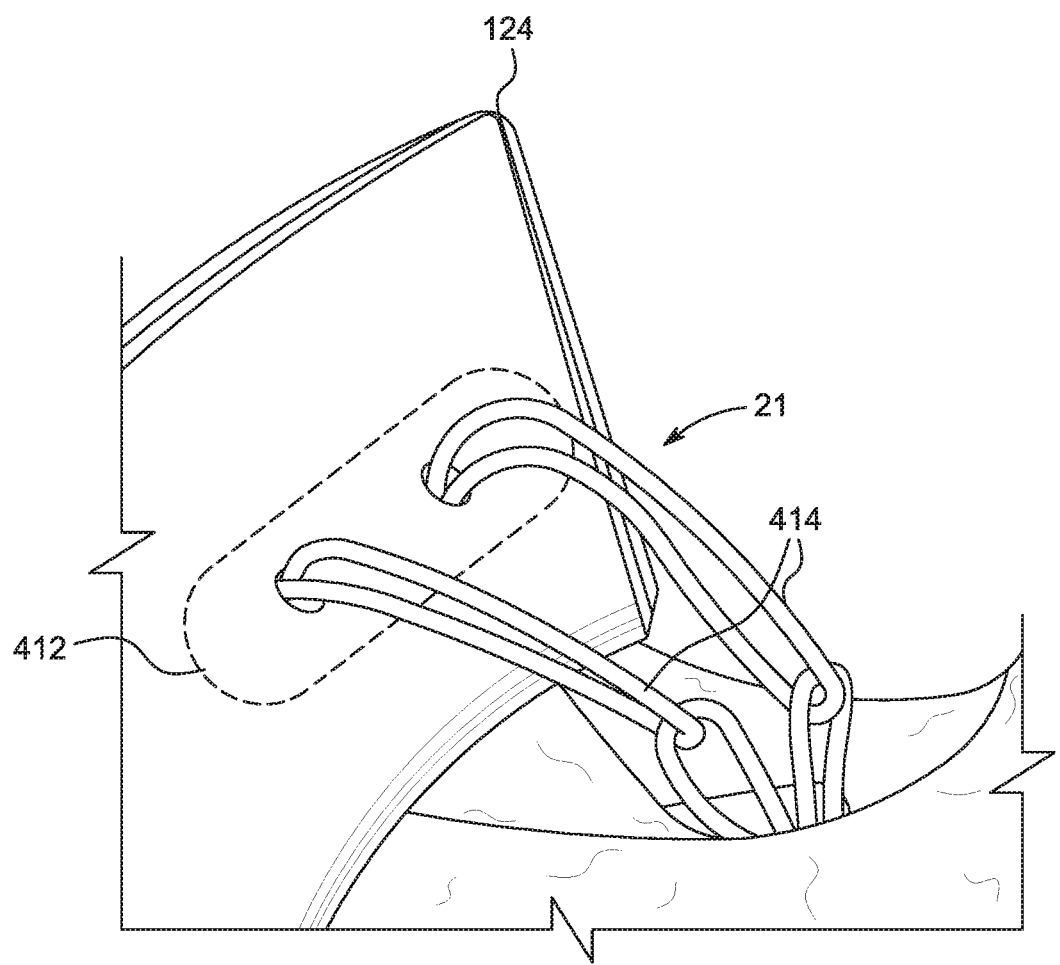
FIGS. 17A and 17B are perspective views of an exemplary embodiment of an anchor securing damaged tissue and reducing the damaged tissue to an anatomical position.
Figure 17B:
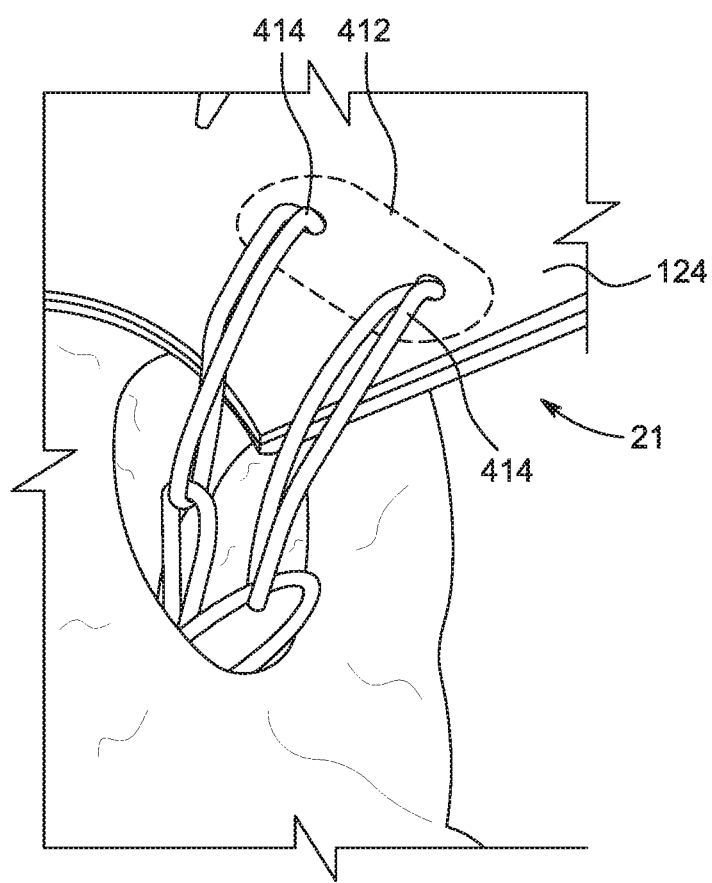

Now referring to FIGS. 17A and 17B, an anchor 21 may be implemented to secure a meniscal root 124. The anchor 21 may have a portion passing through the meniscal root 124 such that the disk is positioned between the meniscal root 124 and the tibia. The securing portion may extend up through the meniscal root and turn back down towards the tibia and the transosseous tunnel. When tension is applied, the meniscal root 124 may be positioned in the correct anatomical position and the securing portion of the anchor 21 may compress a portion of the meniscal root, such that the securing portion rests flush with the remainder of the surface of the meniscus. Thus, the securing portion and the disk are axially spaced from the opposing cartilage tissue of the femur and do not rub or wear the cartilage as the femur and tibia move relative to one another.

Figures 18A, 18B:
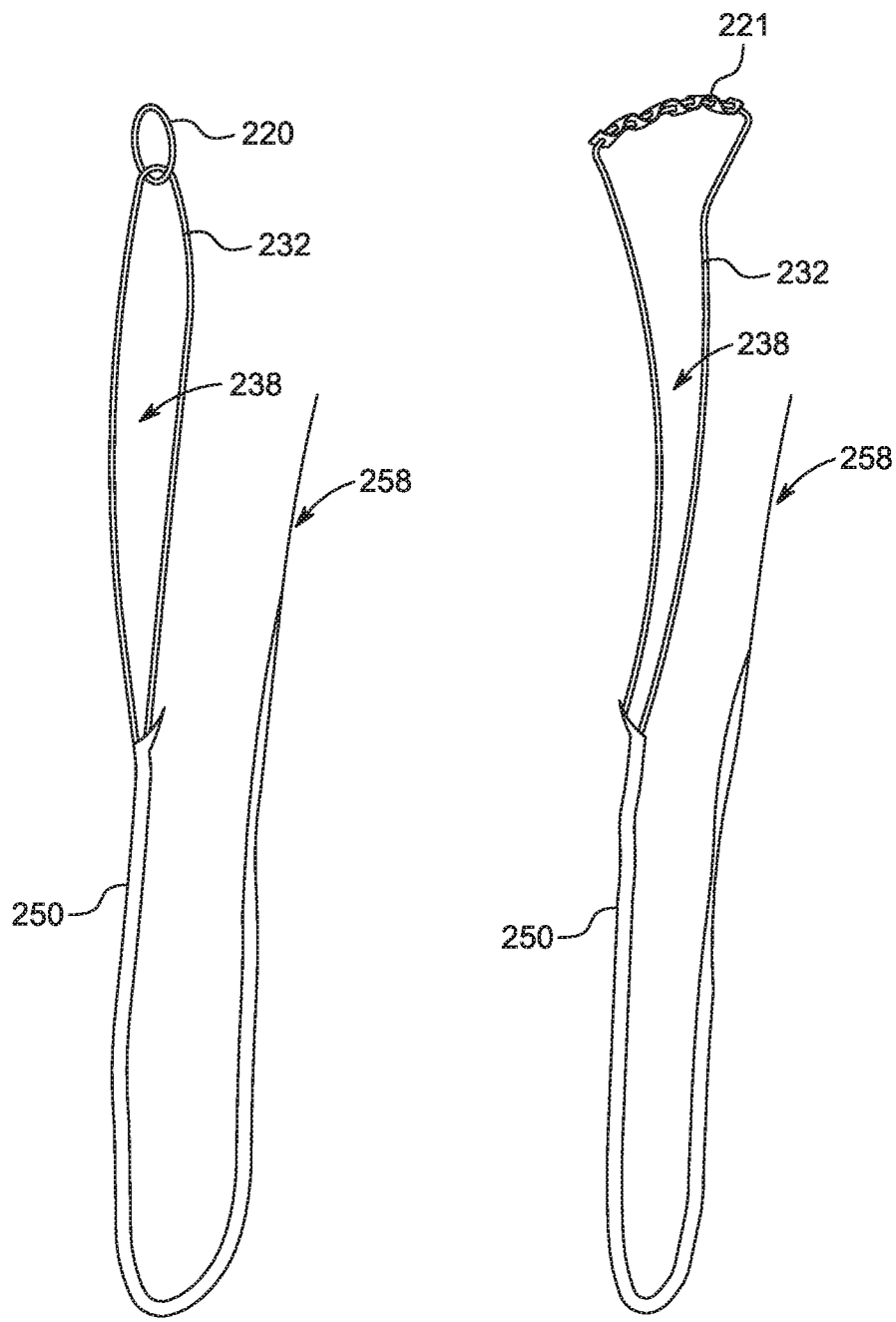
FIGS. 18A and 18B are perspective views of an embodiment of a self-cinching suture construct apparatus having a sheath.
Figure 19A:
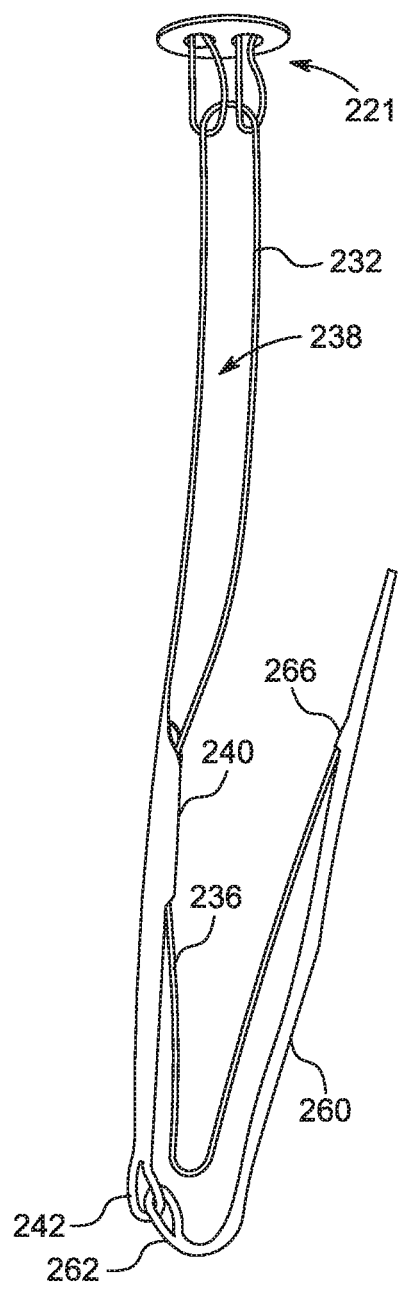
FIGS. 19A and 19B are perspective views of an embodiment of a self-cinching suture construct apparatus having various embodiments of anchors.
Figure 19B:
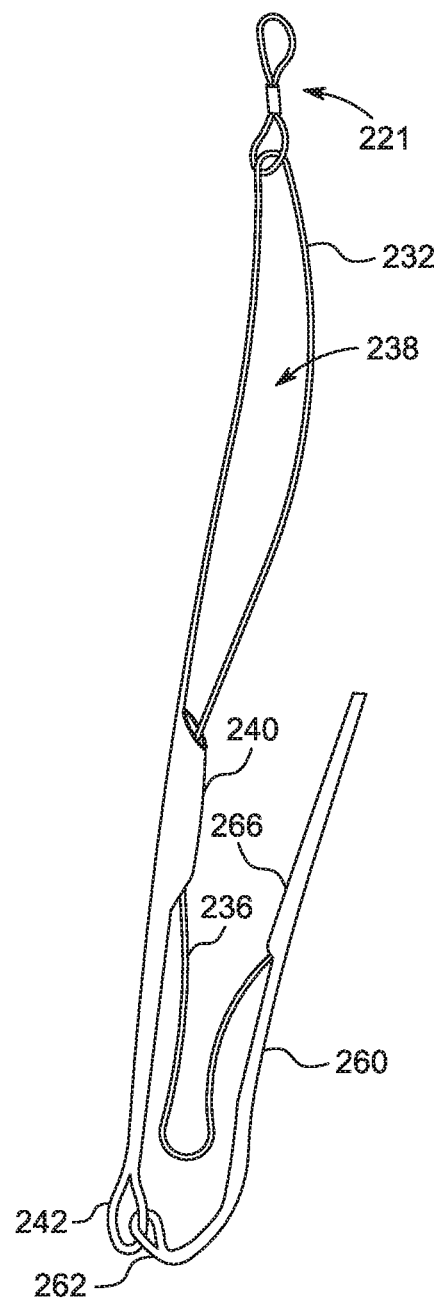

FIGS. 18A and 18B provide exemplary embodiments of a sheathed device using a continuous loops 220 and an anchor 221. FIGS. 19A and 19B depict exemplary embodiments of a suture implementing various embodiments of the anchor 221. FIGS. 18A, 18B, 19A, and 19B could include any of the various disclosed embodiments of the anchor as disclosed herein. Further embodiments of anchors 221 implemented on suture constructs are provided in FIGS. 4C-4I.

Figure 16A:
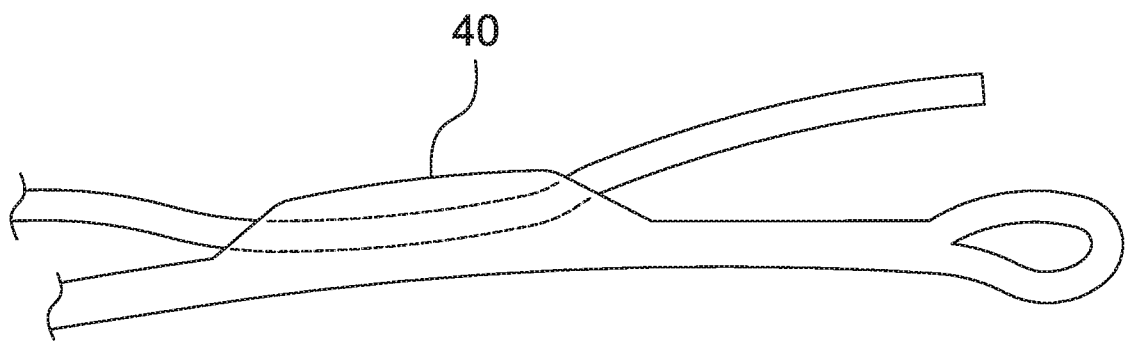
FIGS. 16A and 16B are perspective views of various embodiments of self-cinching sleeves.
Figure 16B:
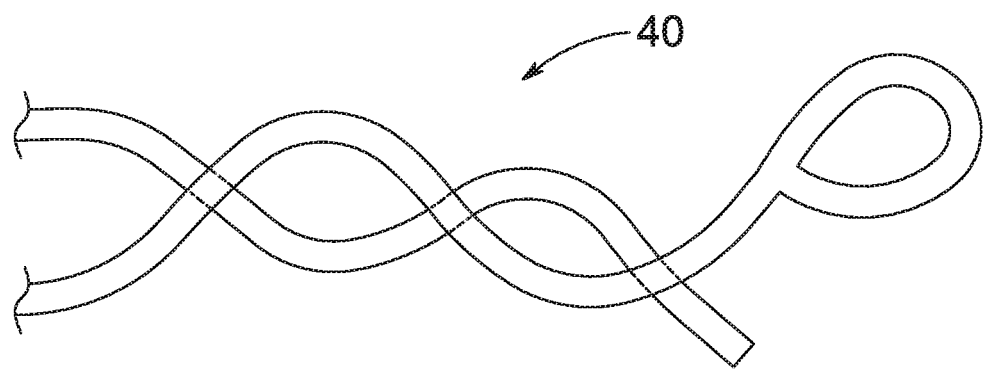

In some embodiments the self-cinching suture sleeve 40 may use an alternative structure to allow the self-cinching suture 32 to prevent the self-cinching suture free end 36 from sliding through the self-cinching suture sleeve 40. For example, the self-cinching suture sleeve 40 may include the suture free end 36 passing back through portions of the self-cinching suture 32 in a cross through embodiment. Exemplary embodiments of each self-cinching suture sleeve 40 are provided in FIGS. 16A and 16B.

Thus, although there have been described particular embodiments of the present invention of a new and useful SELF-CINCHING SUTURE CONSTRUCT APPARATUS, it is not intended that such references be construed as limitations upon the scope of this invention.

What is claimed is:

1. A suture construct apparatus, comprising:
    a self-cinching suture member including a first strand, a second strand, a sleeve defined on the second strand, and a self-cinching suture member fixed loop;
    a sacrificial suture disposed on the self-cinching suture member fixed loop; and
    a sheath removably disposed around at least a portion of the self-cinching suture member, the sheath covering the sleeve defined on the second strand,
    wherein the first strand passes through the sleeve and forms a self-cinching suture member free end, and
    wherein the first strand is axially moveable through the sleeve.

2. The apparatus of claim 1, wherein the suture member comprises braided suture material.

3. The apparatus of claim 2, wherein the suture member comprises a hollow core.

4. The apparatus of claim 1, further comprising a continuous loop forming an opening disposed on the self-cinching suture member.

5. The apparatus of claim 4, wherein the self-cinching suture member passes through the opening formed by the continuous loop.

6. The apparatus of claim 5, wherein the self-cinching suture member forms an adjustable loop between the continuous loop and the sleeve.

7. The apparatus of claim 6, wherein the sheath is removable by sliding the sheath off the self-cinching suture member in a direction away from the continuous loop.

8. The apparatus of claim 7, wherein the continuous loop is configured to form a girth hitch.

9. The apparatus of claim 8, wherein the self-cinching suture member is slidable through the continuous loop.

10. The apparatus of claim 1, further comprising the sacrificial suture including a coupling portion and a sacrificial suture strand.

11. The apparatus of claim 10, further comprising a retaining portion on the sacrificial suture forming an opening in the sacrificial suture strand.

12. The apparatus of claim 11, wherein the self-cinching suture member free end is received in the opening in the retaining portion of the sacrificial suture.

13. The apparatus of claim 12, wherein the sheath covers the sleeve on the self-cinching suture member.

14. The apparatus of claim 13, wherein the sheath comprises a tapered hollow core material.

* * * * *